United States Patent
Gris et al.

(10) Patent No.: US 11,566,038 B2
(45) Date of Patent: Jan. 31, 2023

(54) DEUTERIUM-STABILISED RIBONUCLEIC ACID (RNA) MOLECULES DISPLAYING INCREASED RESISTANCE TO THERMAL AND ENZYMATIC HYDROLYSIS, AQUEOUS COMPOSITIONS COMPRISING STABILISED RNA MOLECULES AND METHODS FOR MAKING SAME

(71) Applicant: deutraMed Solutions Ltd., Collingwood (CA)

(72) Inventors: Pavel Gris, Collingwood (CA); Alfred James Farmilo, Belleville (CA)

(73) Assignee: deutraMed Solutions Ltd.

( * ) Notice: Subject to any disclaimer, the term of this patent is extended or adjusted under 35 U.S.C. 154(b) by 0 days.

(21) Appl. No.: 17/522,946

(22) Filed: Nov. 10, 2021

(65) Prior Publication Data

US 2022/0144876 A1 May 12, 2022

Related U.S. Application Data

(60) Provisional application No. 63/114,418, filed on Nov. 16, 2020, provisional application No. 63/112,370, filed on Nov. 11, 2020.

(51) Int. Cl.
| | | |
|---|---|---|
| *C07H 21/04* | (2006.01) | |
| *C07H 1/00* | (2006.01) | |
| *A61K 39/39* | (2006.01) | |
| *C07H 21/02* | (2006.01) | |
| *A61K 51/04* | (2006.01) | |
| *A61K 39/00* | (2006.01) | |

(52) U.S. Cl.
CPC .............. *C07H 1/00* (2013.01); *A61K 39/39* (2013.01); *A61K 51/0491* (2013.01); *C07H 21/02* (2013.01); *A61K 2039/51* (2013.01); *A61K 2039/53* (2013.01); *A61K 2039/55505* (2013.01)

(58) Field of Classification Search
None
See application file for complete search history.

(56) References Cited

U.S. PATENT DOCUMENTS 9,512,162 B2 * 12/2016 Srivastava ............... C07H 1/00

FOREIGN PATENT DOCUMENTS

| WO | WO1992001673 A1 | 2/1992 |
| WO | WO2019219070 A1 | 5/2019 |
| WO | WO2019158583 A1 | 8/2019 |

OTHER PUBLICATIONS

Zhang et al. ("Advances in mRNA vaccines for infectious diseases." Frontiers in Immunology (2019): 594).*
PCT International Search Report and Written Opinion from PCT/CA2021/051598 dated Jan. 17, 2022.
Chang-Hwei Chen et al., Elucidating Mechanisms of Thermostabilization of Poliovirus by D2O and MgCl2, journal, Jun. 1, 1997, pp. 108-116, vol. 342., No. 1, Archives of Biochemistry and Biophysics.
Cioni, Patrizia and Strambini, Giovanni B., Effect of Heavy Water on Protein Flexibility, journal, Jun. 2002, pp. 3246-3253, vol. 82, Biophysical Journal.
Verheyden, Bart et al., Capsid and RNA stabilisation of the oral polio vaccine, journal, 2001, pp. 1899-1905, Vaccine 19.
Wu, Rong et al., Thermostabilization of live virus vaccines by heavy water (D2O), journal, Mar. 30, 1995, pp. 1058-1063, vol. 13, Vaccine.
Pathak, Arup K. and Bandyopadhyay, Tusar, Water isotope effect on the thermostability of a polio viral RNA hairpin: A metadynamics study, journal, Apr. 27, 2017, The Journal of Chemical Physics.

* cited by examiner

*Primary Examiner* — Kimberly Chong
(74) *Attorney, Agent, or Firm* — Forsgren Fisher; James M. Urzedowski; Daniel A. Tysver

(57) ABSTRACT

The invention relates to the field of RNA stabilisation, and more particularly to the use of deuterium oxide (D₂O) during storage and/or synthesis of RNA molecules. Described herein are deuterium-stabilised ribonucleic acid (RNA) molecules that display an increased resistance to thermal and enzymatic hydrolysis. Also described are aqueous compositions comprising stabilized RNA molecules and methods for making same. The invention is particularly useful for in the manufacture of RNA-based therapeutics, such as mRNA vaccines, to render them less sensitive to temperature fluctuations.

31 Claims, 18 Drawing Sheets

Enzymatic degradation of mRNA
by 0.1ug of RNAse A for 30 sec

C - control
T - Treatment

RNAse A treatment of mRNA
synthesized and stored in H$_2$O

| | |
|---|---|
| 1 | 1 ug/mL |
| 2 | 0.5 ug/mL |
| 3 | 0.1 ug/mL |
| 4 | 0.01 ug/mL |
| 5 | 0.005 ug/mL |
| 6 | 0.0025 ug/mL |
| 7 | 0.001 ug/mL |

| | |
|---|---|
| 1 | 1 ug/mL |
| 2 | 0.5 ug/mL |
| 3 | 0.1 ug/mL |
| 4 | 0.01 ug/mL |
| 5 | 0.005 ug/mL |
| 6 | 0.0025 ug/mL |
| 7 | 0.001 ug/mL |

DEUTERIUM-STABILISED RIBONUCLEIC ACID (RNA) MOLECULES DISPLAYING INCREASED RESISTANCE TO THERMAL AND ENZYMATIC HYDROLYSIS, AQUEOUS COMPOSITIONS COMPRISING STABILISED RNA MOLECULES AND METHODS FOR MAKING SAME

CROSS REFERENCE TO RELATED APPLICATION

The present application claims priority to U.S. Provisional Application Ser. No. 63/112,370 filed on Nov. 11, 2020 and U.S. Provisional Application Ser. No. 63/114,418 filed on Nov. 16, 2020, the content of which is incorporated herein by reference in their entirety.

FIELD OF THE INVENTION

The invention relates to the field of RNA stabilisation, and more particularly to the use of deuterium oxide ($D_2O$) during storage and/or synthesis of RNA molecules.

BACKGROUND OF THE INVENTION

Numerous messenger ribonucleic acid (mRNA) vaccines are being developed currently by various pharmaceutical companies around the world to curb the COVID-19 pandemic. In addition, mRNA therapies are being investigated in a number of medical conditions. This increase of interest in RNA pharmaceutics may help to pave the road for mRNA therapeutics in numerous other fields as well.

However, RNA molecules are inherently unstable and prone to both non-enzymatic and enzymatic hydrolysis, which is a major issue during processing, transport, and storage. One of the most critical factors that needs to be controlled is temperature. All the mRNA vaccines and other mRNA-based therapeutics are sensitive to temperature fluctuations, which can accelerate their degradation. Therefore, there is an urgent need for thermostable mRNA therapeutics.

Some groups have studied a potential role for deuterium oxide ($D_2O$) as a thermal stabilizer. For instance, the use of $D_2O$ has been described for thermostabilizing a live attenuated oral polio vaccine (Wu R. et al., Vaccine, Vol 13, No. 12, pp. 1058-1063 (1995); Newman J. F. E. et al., Vaccine, Vol. 15, pp. 1431-1435 (1995); Milstien J. B et al., *Journal of Infectious Diseases* (1997) doi:10.1093/infdis/175.supplement_1. s247; and Sen A. et al., *Expert Review of Vaccines* (2009) doi:10.1586/erv.09.105, and Pathak A. K. and Bandyopadhyay T., *J. Chem. Phys.* 146, 165104 (2017), doi.org/10.1063/1.4982049). However, the effects were observed with whole attenuated polio viruses and thermostabilization of naked RNA molecules was not studied nor demonstrated. Moreover, the effects of mRNA synthesis in $D_2O$ on the mRNA stability was never addressed and RNA tautomerism was not implicated.

The use of deuterated ribonucleotides during synthesis of RNA molecules has been studied as well. International PCT Patent Publication No. WO 2019/158583 of Ethris GmbH discloses the use of deuterated adenosine, cytidine, guanosine, and/or uridine residues for obtaining polyribonucleotide with reduced immunogenicity. U.S. Patent Application Publication Nos. US 2015/0119665, US 2015/0252071 and US 2015/025207 to ASED LLC. describe, among other things, the synthesis of deuterated nucleobases, deuterated nucleosides, deuterated oligonucleotides, and deuterated RNAs having potential for therapeutic uses. U.S. Pat. No. 5,721, 350 describes the deuterated nucleotide and nucleoside units which are used to synthesize strands of RNA and DNA in NMR applications. International PCT Patent Application Publication No. WO 1992/001673 of Medical Research Council describes the synthesis spin labelled ribonucleosides and ribonucleotides that may comprise deuterium, and uses of these compounds as probes, for example in protein structure and orientation studies. International PCT Patent Application Publication No. WO 2019/219070 of Chia Tai Tianqing Pharmaceutical Group Co. Ltd. describes deuterated oligonucleotides and uses thereof in treating hepatitis B virus infection. However, these patent documents do not teach deuterium as a RNA stabilizer in aqueous solution, let alone increased resistance of RNA molecules to thermal or enzymatic degradation.

Hydrogen bonds play an important role in structural integrity and functionality of most known biomolecules including secondary and tertiary structures of nucleic acids, secondary, tertiary, and quaternary structure of proteins and of biopolymers (Li X. Z., Walker B., and Michaelides A. Proc. Natl. Acad. Sci. U.S.A. (2011) doi:10.1073/pnas.1016653108). Ingle et al. (Nucleic Acids Res. (2014) doi:10.1093/nar/gku934) have found that substituting deuterium for protium at a ribose 5'-carbon produces a kinetic isotope effect on cleavage but this phenomenon appeared to be highly dependent on the nucleotide sequence of the RNA molecule. Hohlffelder et al. (Biomed Res. Int. (2013) doi: 10.1155/2013/592745) demonstrated that $D_2O$ increases transcriptional activity of T7 RNA Pol but any potential effect on stabilization or thermal degradation of RNAs was not investigated nor shown.

Therefore, there is still a need for RNA-based therapeutics that comprises thermostable RNA molecules resistant to temperature fluctuations.

There is also a need for compositions comprising stabilised RNA molecules, including mRNAs and for methods for stabilizing RNA molecules.

There is particularly a need for methods directed at reducing thermal degradation of a RNA molecule, wherein the RNA molecule is synthesized in the presence of deuterium and/or wherein the RNA molecule stored in the presence of deuterium.

The present invention addresses these needs and other needs as it will be apparent from the review of the disclosure and description of the features of the invention hereinafter.

BRIEF SUMMARY OF THE INVENTION

According to one aspect, the invention relates to an aqueous composition comprising stabilised ribonucleic acid (RNA) molecules, said aqueous composition comprising at least one of: (i) RNA molecules and deuterium for stabilising the RNA molecules; and (ii) deuterium-stabilised RNA molecules that have been synthesised in the presence of deuterium. Preferably, the aqueous composition comprises both (i) deuterium in solution and (ii) stabilised RNA molecules that have been synthesised in the presence of deuterium in solution.

Preferably the RNA molecules incorporates deuterium. For instance the RNA molecules may comprise deuterated ribonucleoside tri-phosphates (rNTPs). For instance, the RNA molecules may comprise substitution of protium atoms by deuterium atoms. Particularly, the RNA molecules may comprise a deuterium atom in the 2'OH-group on the ribose sugar moiety.

The stabilised RNA molecules may display increased structural integrity of their primary and/or secondary structure, compared to non-stabilized RNA molecules. They may also display increased resistance to degradation compared to non-stabilised RNA molecules. Preferably, the stabilised RNA molecules display increased resistance to at least one of (i) hydrolysis or degradation by endonucleases, and (ii) thermal degradation. More preferably, the RNA molecules are resistant to thermal hydrolysis (e.g. resistance for one or more days of exposure to 37° C. and/or resistance to challenge at 45° C. or higher).

According to another aspect, the invention relates to an aqueous ribonucleic acid (RNA) composition comprising at least one of: (i) a first aqueous solution comprising deuterium-stabilised RNA molecules, said solution comprising deuterium at a concentration sufficient for stabilising the RNA molecules; and (ii) a second aqueous solution comprising deuterium-stabilised RNA molecules that have been synthesized in the presence of deuterium. Preferably, the aqueous RNA composition comprises both (i) deuterium in solution and (ii) deuterium-stabilised RNA molecules that have been synthesised in the presence of deuterium in solution.

Preferably, the deuterium-stabilised RNA molecules incorporates deuterium. For instance, the deuterium-stabilised RNA molecules may comprise deuterated ribonucleoside tri-phosphates (rNTPs). For instance, the deuterium-stabilised RNA molecules may comprise substitution of protium atoms by deuterium atoms. Particularly, the deuterium-stabilised RNA molecules may comprise a deuterium atom in the 2'OH-group on the ribose sugar moiety.

The deuterium-stabilised RNA molecules may display increased structural integrity of their primary and/or secondary structure, compared to non-stabilized RNA molecules. The deuterium-stabilised RNA molecules may also display increased resistance to degradation compared to non-stabilised RNA molecules. Preferably, the deuterium-stabilised RNA molecules display increased resistance to at least one of (i) hydrolysis or degradation by endonucleases, and (ii) thermal degradation. More preferably, the deuterium-stabilised RNA molecules are resistant to thermal hydrolysis (e.g. resistance for one day or more of exposure to 37° C. and/or resistance to a challenge at 45° C. or higher).

In preferred embodiments, stabilised RNA molecules comprise messenger RNA (mRNA) molecules. Such stabilised RNA molecules may advantageously be components of a vaccine.

According to another aspect, the invention relates to a translation product obtained from translation of a mRNA molecule as defined herein.

According to another aspect, the invention relates to a translation product of a messenger ribonucleic acid (mRNA) molecule, wherein said mRNA molecule consists of a deuterium-stabilised mRNA molecule, and wherein said stabilised mRNA molecule (i) has been contacted with an aqueous solution comprising deuterium and/or (ii) has been synthesised in the presence of deuterium. In embodiments, the translation product is a protein or a polypeptide.

According to another aspect, the invention relates to a method for stabilising a ribonucleic acid (RNA) molecule. In one embodiment the method comprises at least one of: (i) storing the RNA molecule in the presence of deuterium; and (ii) synthesising the RNA molecule in the presence of deuterium. In embodiments, the method compromises consecutive steps of: (a) synthesising said RNA molecule by forward transcription in an aqueous composition comprising deuterium; and (b) storing the synthesized RNA molecule of step (a) in an aqueous solution comprising deuterium.

In embodiments, the synthesising comprises in vitro transcription in an aqueous composition comprising deuterium. In embodiments, the synthesising comprises incorporation of deuterium into the RNA molecule via keto-enol tautomerization. In embodiments the synthesising comprises in vitro transcription (e.g. forward transcription) with deuterated ribonucleoside tri-phosphates (rNTPs). According to this aspect, the presence of deuterium reduces hydrolysis or degradation of the RNA molecule by endonucleases. Also, deuterium reduces thermal degradation of the RNA molecule. Particularly, the presence of deuterium during synthesis of the RNA molecule may reduce the extent of mRNA degradation during transcription.

According to this aspect, a stabilised RNA molecule preferably displays an increased structural integrity of its primary and/or secondary structure, compared to a non-stabilized RNA molecule.

According to another aspect, the invention relates to a method for reducing thermal degradation of a RNA molecule. In one embodiment, the method comprises at least one of: (i) synthesising the RNA molecule in the presence of deuterium; and (ii) storing the RNA molecule in the presence of deuterium. In embodiments, the method comprises consecutive steps of: (a) synthesising the RNA molecule by forward transcription in an aqueous composition comprising deuterium; and (b) storing the synthesized RNA molecule of step (a) in an aqueous solution comprising deuterium. The synthesising may further comprise in vitro transcription with deuterated ribonucleoside tri-phosphates (rNTPs).

According to this aspect, a stored RNA molecule preferably displays reduced hydrolysis or degradation by endonucleases compared to a RNA molecule not synthesized or stored in the presence of deuterium. According to this aspect, a stored RNA molecule displays improved resistance to thermal degradation compared to a RNA molecule not synthesized or stored in the presence of deuterium. According to this aspect, a stored RNA molecule displays increased structural integrity of its primary and/or secondary structure, compared to a non-stabilized RNA molecule.

According to another aspect, the invention relates to a stabilised RNA molecule obtained by any of the methods described herein.

According to another aspect, the invention relates to the use of an aqueous composition as defined herein, or use of a aqueous RNA composition as defined herein, and/or use of a stabilised RNA molecule as defined herein, in the manufacture of a medicament or a vaccine.

According to another aspect, the invention relates to the use of an aqueous composition as defined herein, or use of a aqueous RNA composition as defined herein, and/or use of a stabilised RNA molecule as defined herein, for immunization of a subject in need thereof.

Accordingly, another related aspect of the invention concerns an immunisation method, comprising administering to a subject in need thereof an aqueous composition as defined herein, or an aqueous RNA composition as defined herein, or a stabilised RNA molecule as defined herein. In embodiments, the immunization comprises injecting to the subject a mRNA vaccine.

According to another aspect, the invention relates to a RNA-based therapeutic, said RNA-based therapeutic comprising thermostable RNA molecules which are resistant to temperature fluctuations. In embodiments, the thermostable RNA molecules comprise deuterium-stabilised RNA molecules. In embodiments, the thermostable RNA molecules consists of deuterium-stabilised RNA molecules. Advantageously, the thermostable RNA molecules display resistance to thermal hydrolysis (e.g. resistance for 1 day or more of exposure to 37° C., a and/or resistance a challenge at 45° C. or higher). According to that aspect, resistance to thermal hydrolysis is greater than thermal resistance of corresponding non-stabilised RNA molecules. In embodiments, the thermostable RNA molecules comprise messenger RNA (mRNA) molecules and the RNA-based therapeutic consists of a mRNA vaccine.

According to another aspect, the invention relates to the use deuterium as a thermostabilizer for RNA molecules.

Additional aspects, advantages and features of the present invention will become more apparent upon reading of the following non-restrictive description of preferred embodiments, which are exemplary and should not be interpreted as limiting the scope of the invention.

BRIEF DESCRIPTION OF THE SEVERAL VIEWS OF THE DRAWINGS

FIG. 11A: Post-IVT purification of mRNA was omitted to compare efficiency of IVT with T7 RNA Pol in $H_2O$ and $D_2O$. Solid black line represents mRNA made in $H_2O$ and dashed line mRNA made in $D_2O$. A representative gel electrophoresis is shown in the insert.

Figure 1A:
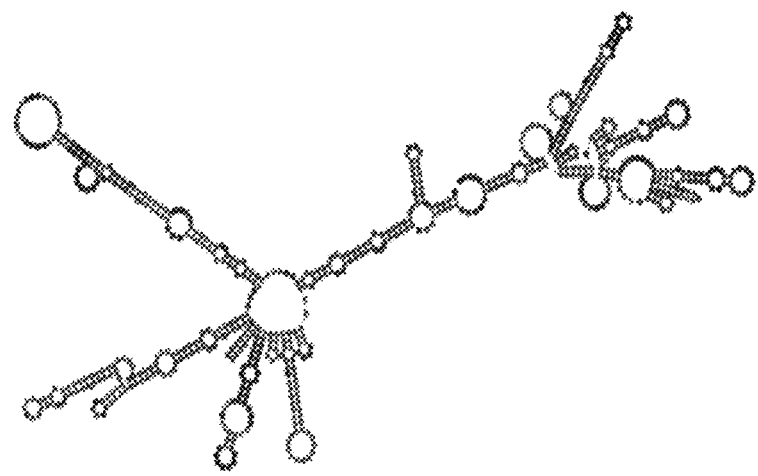
FIG. 1A depicts predicted secondary structures of mRNA molecules synthesized using template P1, in accordance with the Examples described herein.

Further details of the invention and its advantages will be apparent from the detailed description included below.

DETAILED DESCRIPTION OF EMBODIMENTS

In the following description of the embodiments, references to the accompanying figures are illustrations of an example by which the invention may be practiced. It will be understood that other embodiments may be made without departing from the scope of the invention disclosed. Unless defined otherwise, all technical and scientific terms used herein have the same meaning as commonly understood by one of ordinary skill in the art, to which the invention belongs.

General Overview

As is known, the most common cause of mRNA degradation during manufacturing and storage of RNA-based pharmaceuticals is thermal hydrolysis. The present invention addresses this problem, and other problems related to mRNA degradation and stability, by providing deuterium-stabilised RNA molecules, compositions comprising stabilised RNAs, methods for stabilising RNAs, methods for reducing thermal degradation of RNAs, and RNA-based therapeutics comprising such RNA molecules.

Particularly, the present disclosure describes how deuterium can be used in synthesis and/or storage to stabilize RNA molecules, including but not limited to clinically important RNA molecules including messenger RNA, such as mRNA within mRNA vaccines, or other RNA-based therapeutics.

As used herein, the term "deuterium" refers to a stable isotope of hydrogen or "heavy hydrogen" (i.e. $^2$H or D), rather than the common hydrogen-1isotope ($^1$H or H, also called protium) that makes up most of the hydrogen in ambient water ($H_2O$). As used herein, the term "deuterium" or deuterium oxide encompass related terms and molecules such as "deuterium oxide", "$^2H_2O$" and "$D_2O$".

Stabilised RNAs and Compositions

One particular aspect of the invention concerns deuterium-stabilised ribonucleic acid (RNA) molecules and aqueous compositions comprising same.

Advantageously, a deuterium-stabilised RNA according to an embodiment of the invention displays an increased resistance to degradation compared to a corresponding non-stabilised RNA molecule (i.e. a RNA molecule having same sequence or structure). The increased resistance may include resistance to (i) hydrolysis or degradation by endonucleases (e.g. RNAse), and/or resistance to (ii) thermal degradation.

In embodiments of the invention, a deuterium-stabilised RNA displays increased resistance to thermal hydrolysis after 1 day, or 2 days, or 3 days, or 4 days, or 5 days, or 6 days, or 7 days or more of exposure to 37° C., compared to a non-stabilised RNA molecule.

In embodiments of the invention, a deuterium-stabilised RNA displays increased structural integrity of its primary and/or secondary structure, compared to a corresponding non-stabilized RNA molecule.

In embodiments of the invention, a deuterium-stabilised RNA incorporates deuterium.

As used herein, the term "incorporate" or "incorporation" refers to presence of deuterium into the molecular structure of the molecule, and it encompasses integration of the deuterium isotope to the molecule via covalent, hydrogen or other type of bonding or molecular interaction.

In embodiments of the invention, a deuterium-stabilised RNA forms tighter secondary structure in $D_2O$ protecting 2' hydroxyl on the ribose from participating in nucleophilic attack on the phosphodiester bond. In embodiments, the deuterium-stabilised RNA comprises deuterated ribonucleoside tri-phosphates (rNTPs) or utilises the $D_2O$ solvent effect or combination of both.

In embodiments of the invention, a deuterium-stabilised RNA comprises one more deuterium atoms instead of corresponding protium atom(s). In embodiments one or more protium atoms have been replaced by one or more deuterium atoms (e.g. substitution or any other mechanism by which mRNA interacts with $D_2O$ in covalent or non-covalent fashion reducing the extent of thermal or enzymatic hydrolysis).

Figure 18:
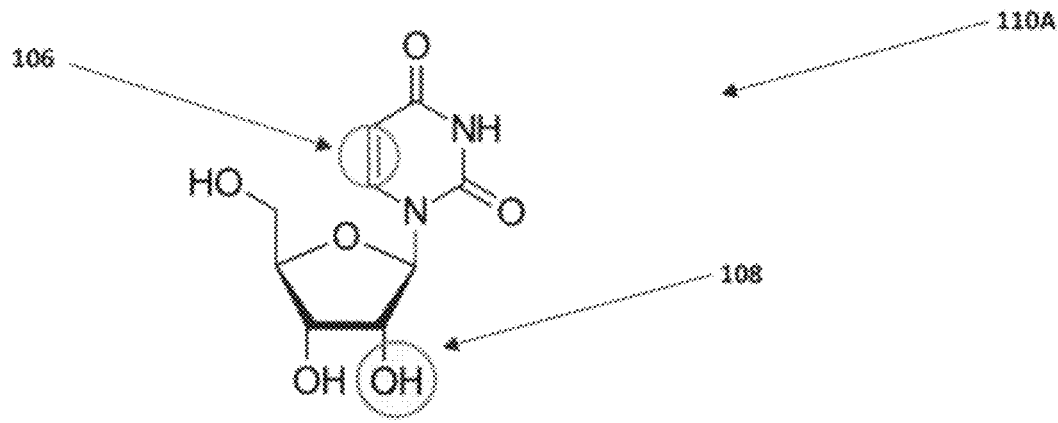
FIG. 18 show the chemical structure of a uridine molecule.

FIG. 18 depicts possible sites for deuteration in accordance with the present invention. For instance, in a uridine molecule (#110A), substitution of protium to deuterium could occur at a double bond in the uracil (5-6 position #106) or at the hydroxyl on the ribose (2' position, #108).

In embodiments, the deuterium-stabilised RNA comprises a deuterium atom in the 2'OH-group on the ribose sugar moiety. In embodiments, the deuterium-stabilised RNA comprise a deuterium isotope in the uracil itself.

In embodiments, the deuterium-stabilised RNA comprises deuterium atom(s) that have been incorporated in the RNA chemical structure during synthesis. For instance, as indicated hereinbefore, the RNA molecule can be synthesized by using deuterated ribonucleoside tri-phosphates (rNTPs).

In accordance with another embodiment, deuterium atom(s) may be incorporated in the RNA molecule during RNA synthesis due to the simple presence of $D_2O$ in solution. In accordance with that embodiment, deuterium incorporation into RNA molecules during RNA synthesis occurs via keto-enol tautomerization. In embodiments, the solution comprising $D_2O$ comprises a deuterium concentration sufficient to favor thermodynamically such incorporation. In embodiments, the aqueous solution comprises a deuterium concentration of at least 5 atom % D, or at least 10 atom % D, or at least 20 atom % D, or at least 30 atom % D, or at least 40 atom % D, or at least 50 atom % D, or at least 60 atom % D, or at least 70 atom % D, or at least 80 atom % D, or at least 85 atom % D, or at least 90 atom % D, or at least 95 atom % D, or at least 96 atom % D, or at least 97 atom % D, or at least 98 atom % D, or at least 99 atom % D, or at least 99.5 atom % D, or at least 99.7 atom % D, or at least 99.9 atom % D. In embodiments, the aqueous solution comprising $D_2O$ comprises deuterium at a concentration of about 5 atom % D to about 100 atom % D, or about 25 atom % D to about 99.9 atom % D, or about 50 atom % D to about 99.9 atom % D, or about 75 atom % D to about 99.9 atom % D, or about 85 atom % D to about 99.9 atom % D, or about 90 atom % D to about 99 atom % D, or about or about 99.7 atom % D.

In other embodiments, the deuterium atom(s) are incorporated in the RNA's chemical structure by contacting an already synthesized RNA molecule (incorporating or not deuterium) with an aqueous solution comprising $D_2O$. In accordance with a particular embodiment, deuterium incorporation into RNA molecules during RNA synthesis occurs via keto-enol tautomerization. In embodiments, the aqueous solution comprising $D_2O$ comprises a deuterium concentration sufficient to favor such incorporation. In embodiments, the aqueous solution comprises a deuterium concentration of at least 5 atom % D, or at least 10 atom % D, or at least 20 atom % D, or at least 30 atom % D, or at least 40 atom % D, or at least 50 atom % D, or at least 60 atom % D, or at least 70 atom % D, or at least 80 atom % D, or at least 85 atom % D, or at least 90 atom % D, or at least 95 atom % D, or at least 96 atom % D, or at least 97 atom % D, or at least 98 atom % D, or at least 99 atom % D, or at least 99.5 atom % D, or at least 99.7 atom % D, or at least 99.9 atom % D. In embodiments, the aqueous solution comprising $D_2O$ comprises deuterium at a concentration of about 5 atom %

D to about 100 atom % D, or about 25 atom % D to about 99.9 atom % D, or about 50 atom % D to about 99.9 atom % D, or about 75 atom % D to about 99.9 atom % D, or about 85 atom % D to about 99.9 atom % D, or about 90 atom % D to about 99 atom % D, or about or about 99.7 atom % D.

The present invention further encompasses aqueous compositions including RNA molecules as defined herein. In embodiments, the aqueous composition consists of a stabilised ribonucleic acid aqueous composition comprising (i) deuterium for stabilising the RNA molecules; and/or (ii) deuterium-stabilised RNA molecules that have been synthesised in the presence of deuterium oxide. In other embodiments, the aqueous composition consists of an aqueous ribonucleic acid (RNA) composition comprising: (i) a first aqueous solution comprising RNA molecules, the solution comprising deuterium at a concentration sufficient for stabilising the RNA molecules; and/or (ii) a second aqueous solution comprising deuterium-stabilised RNA molecules that have been synthesised in the presence of deuterium oxide. In embodiments, the aqueous composition consists essentially of, or alternatively comprises, a stabilised ribonucleic acid aqueous composition comprising (i) deuterium for stabilising the RNA molecules; and/or (ii) deuterium-stabilised RNA molecules that have been synthesized in the presence of deuterium oxide, as well as optional additional components such as RNAase inhibitor(s), enzyme(s), salts dNTPs, etc.

The present invention is not restricted to particular RNA molecules and it encompasses stabilization of various types of RNAs including, but not limited to, total RNA, mRNA, siRNA, shRNA, etc. In embodiments, the RNA molecule consists of a messenger RNA (mRNA) molecule. In embodiments, the mRNA molecule is a component of a therapeutic (e.g. a vaccine or else). The RNA molecule may be obtained from different source, including chemical synthesis, in vitro synthesis, in vivo synthesis, isolated or purified from different sources (e.g. prokaryotic or eukaryotic cells or organisms, viruses, etc.).

Translation Products

Another particular aspect of the invention concerns translation products obtained from translation of a RNA (e.g. mRNA molecule) as defined herein.

In one embodiment of the invention, the translation product consists of the translation product of a mRNA molecule, the mRNA molecule consisting of a deuterium-stabilised mRNA molecule, whereas the stabilised mRNA molecule: (i) has been contacted (e.g. stored) with an aqueous solution comprising deuterium; and/or (ii) has been synthesized in the presence of deuterium.

In embodiments, the translation product is a protein or a polypeptide.

In embodiments, stabilised RNA molecules in accordance with the invention can be integrated into living cells (e.g. in vitro, ex vivo, or in vivo) and they can be transcribed into functional proteins or polypeptides.

Methods of Manufacture and Methods of Use

Additional particular aspects of the invention concern methods for making RNA molecules as defined herein (e.g. deuterium-stabilised RNAs), methods for methods for stabilising ribonucleic acid (RNA) molecules and methods for reducing thermal degradation of RNA molecules.

In embodiments, the method for making deuterium-stabilised RNA molecules as defined herein comprise synthesising the RNA molecules in an aqueous reaction media comprising $D_2O$. In embodiments, the method for making deuterium-stabilised RNA molecules as defined herein comprises synthesising the RNA molecules by using deuterated ribonucleoside tri-phosphates (rNTPs).

In embodiments, the method for stabilising a ribonucleic acid (RNA) molecule comprises at least one of: (i) storing the RNA molecule in the presence of deuterium; and (ii) synthesising the RNA molecule in the presence of deuterium.

In embodiments, the method for reducing thermal degradation of a RNA molecule, comprises at least one of: (i) synthesising the RNA molecule in the presence of deuterium; and (ii) storing the RNA molecule in the presence of deuterium.

In embodiments, and as explained hereinbefore, in accordance with these methods, deuterium atoms may be incorporated in the RNA molecule during RNA synthesis, and/or after RNA synthesis, due to the simple presence of $D_2O$ in solution, for instance but not limited to via keto-enol tautomerization of the RNA molecule.

In embodiments the RNA synthesis is carried out by in vitro transcription (e.g. forward transcription) in an aqueous composition comprising deuterium.

In embodiments these methods comprise at least two consecutive steps of: (a) synthesising the RNA molecule by forward transcription (e.g. in vitro transcription) in an aqueous composition comprising deuterium; and (b) storing the synthesized RNA molecule of step (a) in an aqueous solution comprising deuterium. In embodiments, the synthesising step comprises forward transcription (e.g. in vitro transcription) with deuterated ribonucleoside tri-phosphates (rNTPs).

In accordance with these methods, the presence of deuterium in the reaction media and/or in the RNA storage media provides one or more of the following benefits:
  i. reduction of hydrolysis or degradation of the RNA molecule by endonucleases (e.g. reduce affinity of RNA to endonucleases or else)
  ii. reduction of thermal degradation (e.g. hydrolysis) of the RNA molecule, for instance reduction of degradation over 0° C. such as at 0-45° C., or at 37° C. or a challenge at 45° C. or higher;
  iii. reduction of mRNA degradation during transcription;
  iv. increased structural integrity of the primary and/or secondary structure of the deuterium-stabilised RNA molecule, compared to a non-stabilized RNA molecule;
  v. increased structural integrity of the tertiary and/or quaternary structure of the deuterium-stabilised RNA molecule, compared to a non-stabilized RNA molecule;
  vi. increasing RNA half-life;
  vii. increasing bioavailability of the RNA molecule for its substrate (i.e. ribosomes, other RNA molecules, etc.).

Accordingly, the present invention further encompasses the use of deuterium as a thermostabilizer when used as a solvent. In embodiments, deuterium is used as a thermostabilizer for RNA (e.g. mRNA, siRNA, shRNA, etc.) and its thermostabilizing activity is particularly useful for reducing hydrolysis and/or degradation of RNA molecules, including, but not limited to, during extended exposures (e.g. 1 day, or 2 days, or 3 days, or 4 days, or 5 days, or 6 days, or 7 days or more) to 37° C., and/or during a challenge at 45° C., or at 50° C., or at 55° C., or at 60° C., or at 65° C., or at higher temperatures. The present invention further encompasses the use of deuterium for RNA stability during renaturation process when the temperature decreases. In embodiments deuterium is used as a thermostabilizer for enzymes and/or for enzymatic activity.

Therapeutical Applications

The RNA molecules in accordance with embodiments of the present invention may find numerous applications as research tools and therapeutics (e.g. RNA chemistry, nanofabrication, delivery systems, immunization, etc.).

Potential therapeutic applications of the RNA molecules of the invention include, but are not limited to, immunization against pathogens, cancer immunotherapies, infectious disease vaccines, allergy tolerization, protein-replacement and supplementation therapies, genome engineering and genetic reprogramming.

Accordingly, an additional aspect of the invention concerns RNA-based therapeutics comprising aqueous ribonucleic acid (RNA) compositions as defined herein and/or comprising stabilised RNA molecules as defined herein (e.g. mRNA, siRNA, shRNA, etc.). In one embodiment, the RNA-based therapeutic comprises thermostable RNA molecules resistant to temperature fluctuations. In embodiments, the thermostable RNA molecules display resistance to thermal hydrolysis after 1 day, or 2 days, or 3 days, or 4 days, or 5 days, or 6 days, or 7 days or more of exposure to 37° C. In embodiments, the thermostable RNA molecules display resistance to thermal hydrolysis after a challenge at 45° C., or at 50° C., or at 55° C., or at 60° C., at 65° C. In embodiments, the above resistance to thermal hydrolysis is greater than thermal resistance of corresponding non-stabilised RNA molecules. In embodiments, the RNA molecule consists of a messenger RNA (mRNA) molecule.

In embodiments, aqueous compositions and/or stabilised RNA molecules as defined herein are used in the manufacture of a therapeutical product (e.g. a medicament, an active pharmaceutical ingredient and/or a vaccine) and/or for research purposes. In embodiments, aqueous compositions as defined herein and/or stabilised RNA molecules as defined herein are for administration to a subject in need thereof (e.g. for injection of the RNA to the subject). The term "subject" includes mammals in which administration of RNA molecules is desirable. The term "subject" includes domestic animals (e.g. cats, dogs, horses, pigs, cows, goats, sheep), rodents (e.g. mice or rats), rabbits, squirrels, bears, primates (e.g., chimpanzees, monkeys, gorillas, and humans), wild animals such as those living in zoos (e.g. lion, tiger, elephant, and the like), and transgenic species thereof. Preferably, the subject is a human, more preferably a human patient in need of treatment.

In embodiments, aqueous compositions as defined herein and/or stabilised RNA molecules as defined herein are used for immunization and/or for other therapeutic-related intervention(s) of a subject in need thereof (e.g. for injection of the RNA to the subject).

In embodiments, the vaccine is a mRNA vaccine. In embodiments, the vaccine is for immunization against a viral or other pathogen. In embodiments, the vaccine is a vaccine against Covid-19.

Those skilled in the art will recognize, or be able to ascertain, using no more than routine experimentation, numerous equivalents to the specific procedures, embodiments, claims, and examples described herein. Such equivalents are considered to be within the scope of this invention, and covered by the claims appended hereto. The invention is further illustrated by the following examples, which should not be construed as further or specifically limiting.

EXAMPLES

This section provides examples set out to evaluate the effects of mRNA secondary structure, rNTPs deuteration and mRNA synthesis in deuterated environment on the subsequent mRNA stability to thermal hydrolysis and functionality in vitro and in vivo.

The present examples demonstrate, among other things, that synthesis and storage of mRNA in deuterium oxide improves mRNA resistance to thermal and enzymatic hydrolysis. Particularly, the present examples focus on the effect of synthesis and storage of mRNA in $D_2O$ on the mRNA stability during different temperature challenges. To the best of the inventors' knowledge, this is the first study to address the mRNA stabilization by deuterium oxide in comprehensive way.

Materials and Methods

Plasmids

Two plasmids with pCDNA3.1 backbone were engineered to contain sequences that can be transcribed to make mRNA which is coded to make Green Fluorescent Protein (GFP). The GFP mRNA sequences that differ in their GC content, but code for the same amino acids. The two templates were used to test the hypothesis that different GC content will affect mRNA stability in $D_2O$ due to the differences in the mRNA secondary structure. The constructs contained CMV-T7-SP6-GFP regions. The GFP RNA derived from plasmid 1/P1 had GC % of 38.8% and the GFP RNA derived from plasmid 2/P2 had GC % of about 62.2%.

The GFP regions of the plasmids were analysed for secondary structures using the prediction tool RNAfold WebServer™ form University of Vienna. The minimum free energy (MFE) of P1 was −141.30 kcal/mol and P2 was −256.3 kcal/mol.

Bacterial Transformation and Culture

Competent E. coli cells (Fisher Scientific OMNIMAX2™ #C854003) and plasmid DNA mixture was incubated on ice for 20-30 mins and thereafter subjected to heat shock transformation by being placed in a 42° C. water bath for 45 secs and on ice for 2 minutes. Luria Broth™ (LB) media (EMD Cat #1.10285.0500) without antibiotic was added to the bacteria and grown in 37° C. shaking incubator for 45 min at 350 rpm. The transformed cells were plated on LB agar (EMD Cat #1.10283.0500) containing Ampicillin (50 ug/mL) and incubated at 37° C. overnight.

From the LB agar plate, 3-4 colonies were picked and inoculated into liquid LB media containing Ampicillin at 50 ug/mL and incubated at 37° C. for 12-18 hr in a shaking incubator at 350 rpm.

A small amount of the overnight culture was added to 50% glycerol (Fisher Scientific™ Cat #M-12585) in a cryovial and frozen at −80° C. for future use.

Plasmid DNA Isolation 500 mL of the overnight culture was used for the plasmid purification by QIAGEN™ Plasmid Maxi kit (Cat #12161) as described by the manufacturer. In this method, bacterial lysates were cleared by centrifugation. The cleared lysate was then loaded onto the anion-exchange tip where plasmid DNA was selectively bound under appropriate low-salt and pH conditions. RNA, proteins, metabolites, and other low-molecular-weight impurities were removed by a medium-salt wash, and pure plasmid DNA was eluted in high-salt buffer. The DNA was concentrated and desalted by isopropanol precipitation, collected by centrifugation, and resuspended in TE buffer.

Linearization and Clean-Up of Digested Plasmid DNA

The purified DNA was quantified using Nanodrop™ spectrophotometer (ThermoFisher Scientific) and 10 ug of DNA was linearized in a 100 ul reaction volume, using restriction enzyme XbaI (New England Biolabs Cat #R0145S) with cut site: T/CTAGA. The Serial Cloner™ software, version 2.6.1 was used to identify the restriction enzyme with a single cut site in the plasmid:

```
5’ . . . T▼C T A G A . . . 3’

3’ . . . A G A T C▲T . . . 5’
```

The restriction digestion mixture was incubated at 37° C. for 1 hour followed by heat inactivation at 65° C. for 20 minutes. This was then cleaned-up using silica membrane based QIAquick™ PCR purification kit that binds DNA in high-salt buffer and elution with low-salt buffer. The protocol uses a bind-wash-elute method. The linearized DNA product was then run on 1.5% agarose gel and the product size corresponded to 1200 base pairs on the 100 bp DNA ladder (New England Biolabs Cat #N3231S). The linearized DNA was quantified using nanodrop and 1-1.5 ug was taken for in vitro transcription.

In Vitro Transcription

Three different IVT protocols were set-up for each of the plasmid by using either normal NTPs (New England Biolabs cat #E2040S), a mix of partially deuterated NTPs (Cambridge Isotope Laboratories Cat #DLM—7862) or deuterated UTP (Millipore Sigma Cat #902454-10MG) mixed with regular ATP, CTP and GTP. The template DNA was mixed with nucleotides and T7 RNA polymerase mix of the HiScribe™ IVT kit (New England Biolabs, Cat #E2040S). The reaction mixture was mixed thoroughly, pulse-spun and incubated at 37° C. for 2 hours. Template DNA was removed by setting up a reaction with DNase I (Qiagen cat #79254) at 37° C. for 15 minutes. The synthesized RNA was then purified using New England Biolab's Monarch™ RNA Cleanup Kit (Cat #T2050). For analysis of mRNA degradation and large molecular weight fragment contamination this was modified as follows. The IVTs were performed for 4 hours at 37° C. and 400 ng of mRNA was immediately resolved on 1.5% agarose gel. The data were acquired with Image J and intensities of entire lanes were plotted in Python™.

The RNA was eluted into 50 uL of $H_2O$ or $D_2O$. The elution in $H_2O$ was used to test the isotope kinetic effect exclusively while elution on $D_2O$ was used to evaluate combined solvent and isotope kinetic effects. Effect of mRNA synthesis in fully deuterated environment on the mRNA stability was tested by synthesising mRNA and storing in $D_2O$ followed by thermal hydrolysis.

Thermal Degradation Test

RNA aliquots (400 ng) were subjected to 45° C. and 65° C. for 10 min, 60 min and 18 hours in a thermocycler. Additionally, the mRNAs were subjected to the 37° C. treatment for 2, 3, 5, and 7 days. RNA was resolved on 1.5% agarose gel stained with ethidium bromide for visualization. Markers such as 100 bp DNA ladder (New England Biolabs Cat #N3231S) and ssRNA ladder (New England Biolabs Cat #N0362S) were used for molecular size estimation. The effect of the mRNA secondary structure on the stabilization by $D_2O$ measured as degree of preservation.

RNA Integrity Analyses

ImageJ™ software was used for quantification of the RNA signal form agarose gel images. A rectangular region of interest was positioned to cover a maximum amount of signal in each lane. Without altering the region of interest, pixel values for each lane were recorded. Python™ programming was used for further analysis and interpretation, using a custom algorithm: the area under the signal curve (AUC) normalized to the signal mean was used to estimate the intensity of the signal at the expected 850 bp region and in the degradation zone. The shift of the signal intensity from the 850 bp to the degradation zone was denoted as peak shift. In the gels where a signal shift was not detected, the value of the shift was denoted as 1. Degree of RNA preservation was defined as $Deg\_P = AUC_{Exp} \times Mean_{Exp}/AUC_{control} \times Mean_{Control}$.

In an experiment evaluating the effect of synthesis in $D_2O$ on mRNA integrity and T7 Pol specificity, the area under the curve corresponding to the degradation zone (below the template-specific signal) was used. The beginning of the degradation zone was arbitrarily set at one-third of the peak height, where the spread of the curve started to become prominent. Due to the notable background signal in the high molecular weight contamination zone (above the template-specific signal), we chose to use the width of the template-specific signal peak at ⅓ of the peak height (i.e. after degradation zone) to denote the peak width. A wide peak would indicate an increased occurrence of mRNA products with different molecular weights.

Furthermore, undegraded control RNA and RNA subjected to thermal hydrolysis were screened using Agilent Bioanalyzer 2100™ for RNA integrity numbers and analysis of the smear/degradation zone.

Capping of mRNA and In Vitro Translation

The in vitro transcribed RNA was capped afterwards to facilitate initiation of translation and translational competence for downstream in vitro translation experiment. The capping was done using New England Biolabs™ capping kit (Cat #M2080), which utilizes vaccinia virus capping enzyme (VCE), GTP and the methyl donor, SAM.

The Retic Lysate IVT Kit™ from Ambion (Cat #AM1200) was used to carry out in vitro translation. Capped RNA templates (1 ug) were mixed with 20× translation mix, Met amino acid and reticulocyte lysate in a 50 uL reaction volume. A no-template control was used to subtract the background fluorescence. The mixture was then incubated at 30° C. for 90 minutes. The product was transferred to Optiplate™ (PerkinElmer cat #6005270) for reading in fluorescence plate reader (Berthold Tech Tristar 2™) at an excitation wavelength of 485 nm and emission wavelength of 530 nm.

In Vivo Translation of GFP IVT mRNA

It has been demonstrated that naked (and non-deuterated) mRNA injected into mice results in translation of the cognate protein it codes for, this phenomenon constituting the basis for mRNA therapeutics. In this example, we proceeded to validate that mRNA synthesized and stored in $D_2O$ can be translated into a functional protein when injected into mice. 400 uL of in vitro transcribed mRNA (10 ug/uL) was injected intraperitoneally into C57BL/6 mice (Jackson Laboratory-Bar Harbor, Me., USA) to assess in vivo translation of GFP. After in vitro transcription in $D_2O$, mRNA was resuspended in $D_2O$ at 1.2 mg/ml. C57BL6 mice of twenty-week-old were injected interperitoneally with 0.5 ml of mRNA solution or $H_2O$ as a control. After 24 hrs, mice were euthanized, and their spleens were dissected and homogenized to obtain a single cell suspension, which was analyzed by flow cytometry. Murine splenocytes were prepared in cold phosphate-buffered saline (PBS) (Multicell Cat #311-010-CL). Flow cytometry data were collected (Cyto-FLEX™ Beckman Coulter, Brea, Calif., USA) and analyzed using CytExpert™ (Version 2.4.0.28, Beckman Coulter Inc.). FITC (Fluorescein-5-isothiocyanate) channel with an excitation peak at 491 nm and an emission peak at 516 nm were used to analyze GFP. At least 100 000 cells were gated on the GFP positive cells. Background fluorescence was set as 0.01% positive cells using control. The established gates were applied to samples from mRNA-treated animals. The result confirms a robust expression of the mRNA template.

Statistical power analysis.

To evaluate the validity of the sample size we used power analysis with significance level $\alpha=0.05$.

Statistical power analysis of mRNA synthesis in $H_2O$ and $D_2O$ experimental data. Power analysis only considers the scenario when true null hypothesis is correctly rejected (true positive). It calculates probability of finding the difference when there is a difference between means of two populations. High probability from 0.8 to 1 suggest the ability of detection of true difference. Statistical power depends on effect size, variability of the data that depends on the number of observations, and confidence/significance value $\alpha$. Value $\alpha$ defined by the research as a cut of desirable statistical significance. The most widely accepted level of statistical significance accepted in the peer review scientific publication and the court of law of majority of the countries including USA and Canada is 0.05.

Therefore, given the pilot data, power analysis gives information about number of samples required to demonstrate statistically (at the level $\alpha$) significant differences between means of two population. Also, Power analysis provides the information about statistical power in existing data.

Figure 1B:
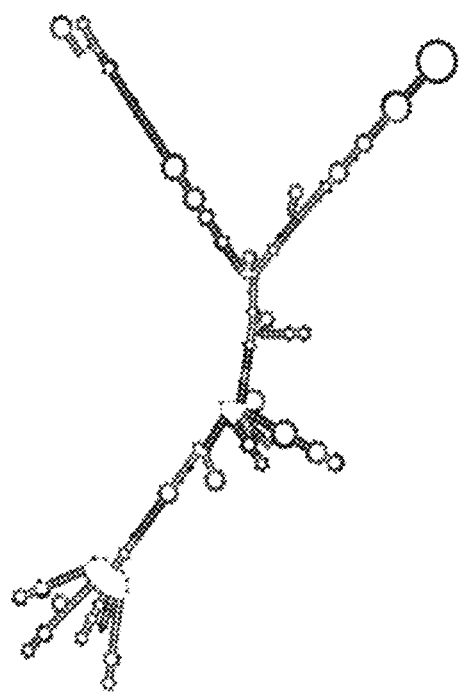
FIG. 1B depicts predicted secondary structures of mRNA molecules synthesized using template P2, in accordance with the Examples described herein.

Example 1: Synthesis and Storage of mRNA in $D_2O$ Protects mRNA from Thermal and Enzymatic Hydrolysis and Improves the Transcription Efficiency Predicted secondary structures of mRNA molecules synthesized using template P1 and template P2 is shown in FIG. 1A and FIG. 1B. For Template P1 MFE: −141.30 kcal/mol, GC: 38.8% and for template P2 MFE: −256.30 kcal/mol, GC: 62.3%. MFE denotes minimal free energy. P2 mRNA with higher GC content demonstrates a more structured and stable secondary structure as expected.

To test the effect of synthesis and storage of mRNA in $D_2O$ on the mRNA stability during different temperature, this study focused on the effect of synthesis and storage of mRNA in $D_2O$ on the mRNA stability during different temperature a series of molecular tools were used in different temperature challenge paradigms, as shown in Table 1.

Figure 2A:
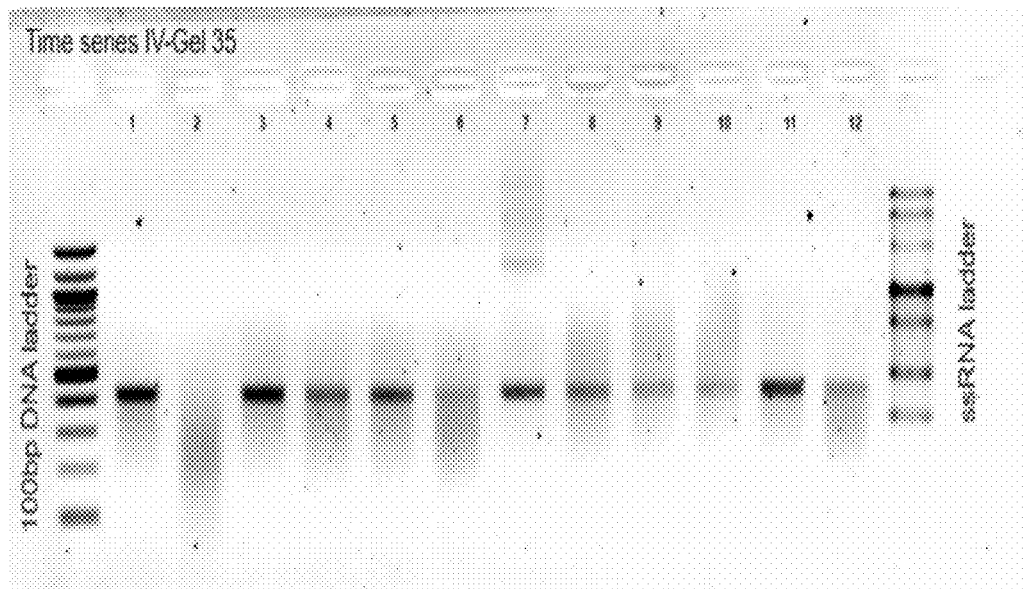
FIGS. 2A and 2B are pictures of an agarose gel showing electrophoresis of mRNA stored at 37° C. for 2 days in accordance with the examples described herein. mRNA was synthesized using P1 and P2 templates synthesized and stored in light water (FIG. 2A) or synthesized and stored in $D_2O$ (FIG. 2B), in accordance with the Examples described herein. Description of the lanes is found in Table 1 hereinafter.
Figure 2B:
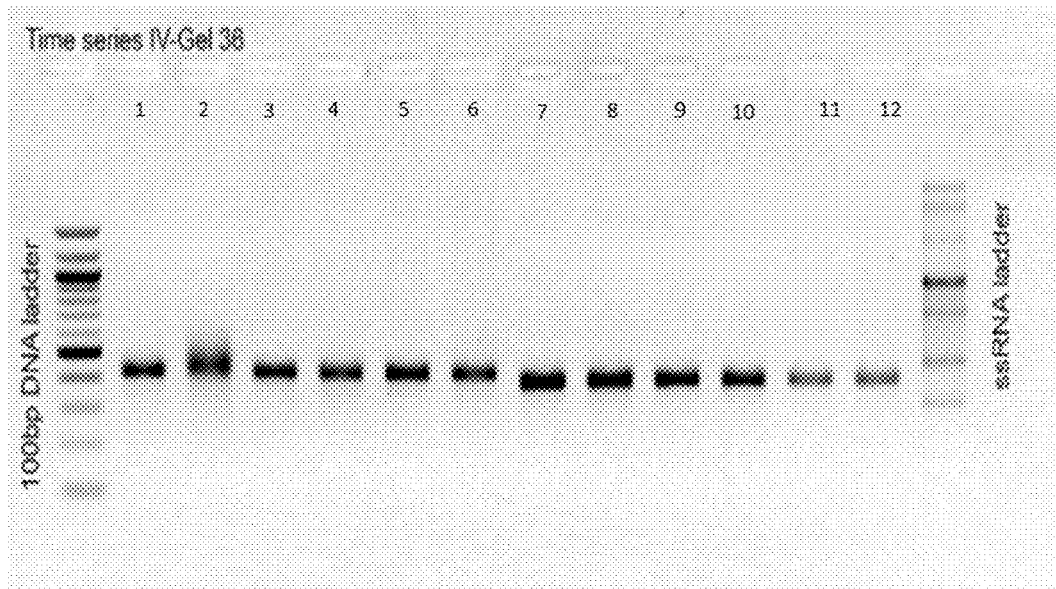

Results of the thermal degradations tests are shown in FIGS. 2A and 2B. The decrease in template-specific signal (850 bp) in the mRNAs exposed to 37° C. for 48 hours that were produced and stored in the light water is prominent (FIG. 2A). In the mRNAs that were produced and stored in $D_2O$ this trend was not observed (FIG. 2B). We denote the diffused signal below 850 bp as degradation zone because the products of mRNA degradation are of smaller molecular weight and travel farther in the gel. The degradation zone signal was higher in the mRNAs that were produced and stored in light water than in the mRNAs that were produced and stored in $D_2O$.

Note that there are mRNA fragments of size larger than 850 bp. They are detected as diffuse signal of molecular weight greater than the specific signal (850 bp in this study) This effect is commonly observed when T7 RNA polymerase is used and are attributed to the 3' transcript extension. There were fewer 3' extension products in mRNA that were produced and stored in $D_2O$.

From the data shown on FIGS. 2A-2B, it appears that $D_2O$ has a dual effect on mRNA: 1) it protects it from the thermal hydrolysis, demonstrated as fewer small fragments and 2) improves the specificity of T7 RNA Pol, demonstrated as fewer higher molecular weight products. To quantify and statistically analyze the data obtained from the gel electrophoresis experiments we designed the approach illustrated in FIG. 3.

Figure 3A:
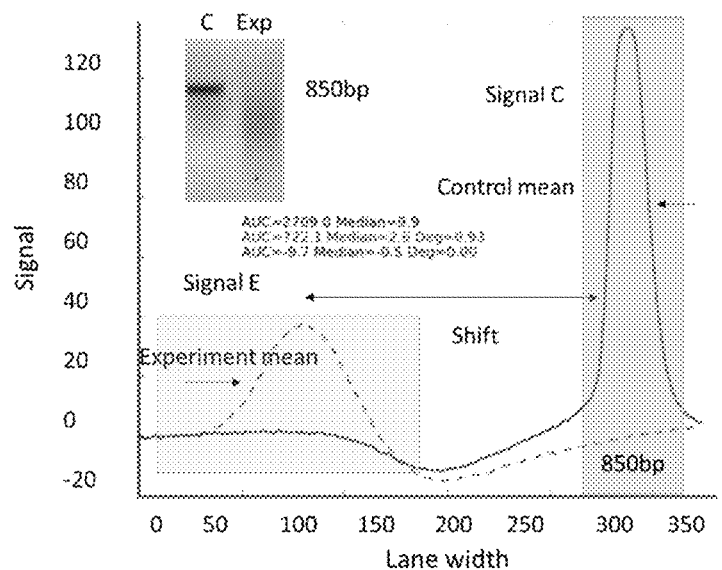
FIGS. 3A and 3B are graphs showing distribution curves used for assessing mRNA degradation, in accordance with the Examples described herein.
Figure 3B:
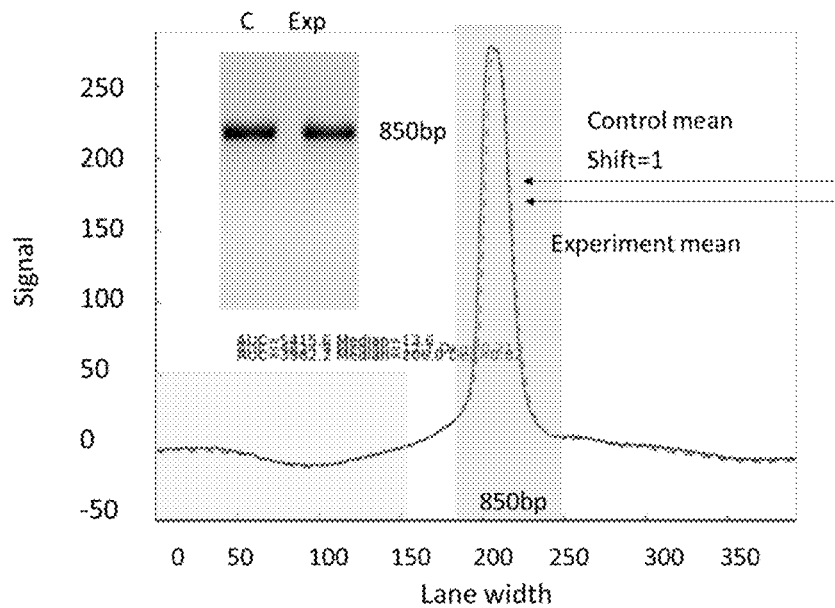

A strategy was designed for assessing mRNA degradation. mRNAs were resolved using 1.5% agarose gels and stained with Et-Br as described in Materials and Methods section. The data were acquired using Image J™ and processed with Python™ using proprietary script. Briefly, mRNA is traveling from the negative to positive terminal of the gel electrophoresis system. As it travels it gets distributed by size. The largest and the heaviest molecules travel slow, and the small ones travel fast. Because the gel is stained with Et-Br, mRNA would fluoresce under the UV light. The intensity of fluorescence is used as proxy for mRNA abundance. Therefore, the sum of fluorescent signals in the gel can be represented as distribution (FIGS. 3A and 3B).

The height of the peak of the signal intensity distribution was denoted as signal magnitude. The mean of the signal magnitude was denoted as signal mean. The area under the signal curve (AUC) normalized to the signal mean was used to estimate the intensity of the signal at the 850 bp and in the degradation zone. The shift of the signal intensity from the 850 bp to the degradation zone was denoted as peak shift (FIG. 3A). In the gels where signal shift was not detected the value of the shift was denoted as 1 (FIG. 3B). The degree of RNA preservation was defined as $Deg\_P = AUC_{Exp} \times Mean_{Exp}/AUC_{control} \times Mean_{Control}$.

TABLE 1

Molecular tools used to study the effect of $D_2O$ on mRNA resistance to thermal hydrolysis in different temperature challenge paradigms

| | Code name | Description |
|---|---|---|
| 1 | Plasmid 1 NTP-H | GC 38.8% regular rNTPs synthesis and storage in $H_2O$ |
| 2 | Plasmid 1 dNTP-H | GC 38.8% deuterated rNTPs synthesis and storage in $H_2O$ |
| 3 | Plasmid 1 mUTP-H | GC 38.8% deuterated Uracil synthesis and storage in $H_2O$ |
| 7 | Plasmid 1 NTP-D | GC 38.8% regular rNTPs synthesis and storage in $D_2O$ |
| 8 | Plasmid 1 dNTP-D | GC 38.8% deuterated rNTPs synthesis and storage in $D_2O$ |
| 9 | Plasmid 1 mUTP-D | GC 38.8% deuterated Uracil synthesis and storage in $D_2O$ |
| 4 | Plasmid 2 NTP-H | GC 62.3% regular rNTPs synthesis and storage in $H_2O$ |
| 5 | Plasmid 2 dNTP-H | GC 62.3% deuterated rNTPs synthesis and storage in $H_2O$ |
| 6 | Plasmid 2 mUTP-H | GC 62.3% deuterated Uracil synthesis and storage in $H_2O$ |
| 10 | Plasmid 2 NTP-D | GC 62.3% regular rNTPs synthesis and storage in $D_2O$ |
| 11 | Plasmid 2 dNTP-D | GC 62.3% deuterated rNTPs synthesis and storage in $D_2O$ |
| 12 | Plasmid 2 mUTP-D | GC 62.3% deuterated Uracil synthesis and storage in $D_2O$ |

For the mRNA stability over time experiments mRNAs were synthesised and stored in $H_2O$ and $D_2O$ and then incubated at 37° C. for 2, 3, or 7 days to extend the duration of the experiment. The mRNAs were resolved using 1.5% agarose gel electrophoresis. The results of these experiments are depicted in FIGS. 4A and 4B.

Figure 4A:
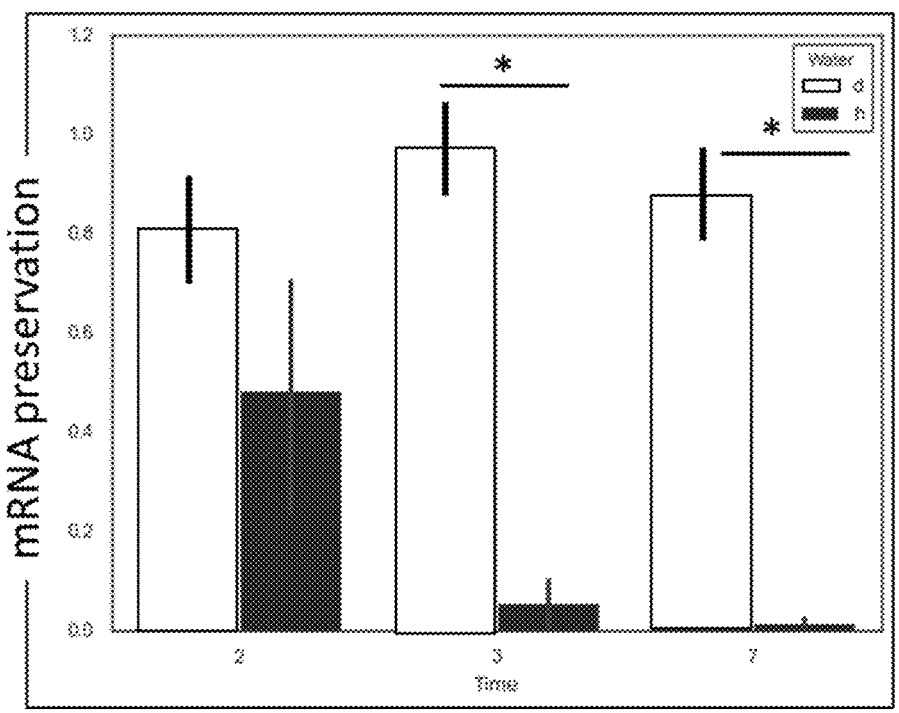
FIGS. 4A and 4B are bar graphs depicting the effect of synthesis and storage of mRNA in $D_2O$ on mRNA preservation at 37° C. for 2, 3 or 7 days, in accordance with the Examples described herein.
Figure 4B:
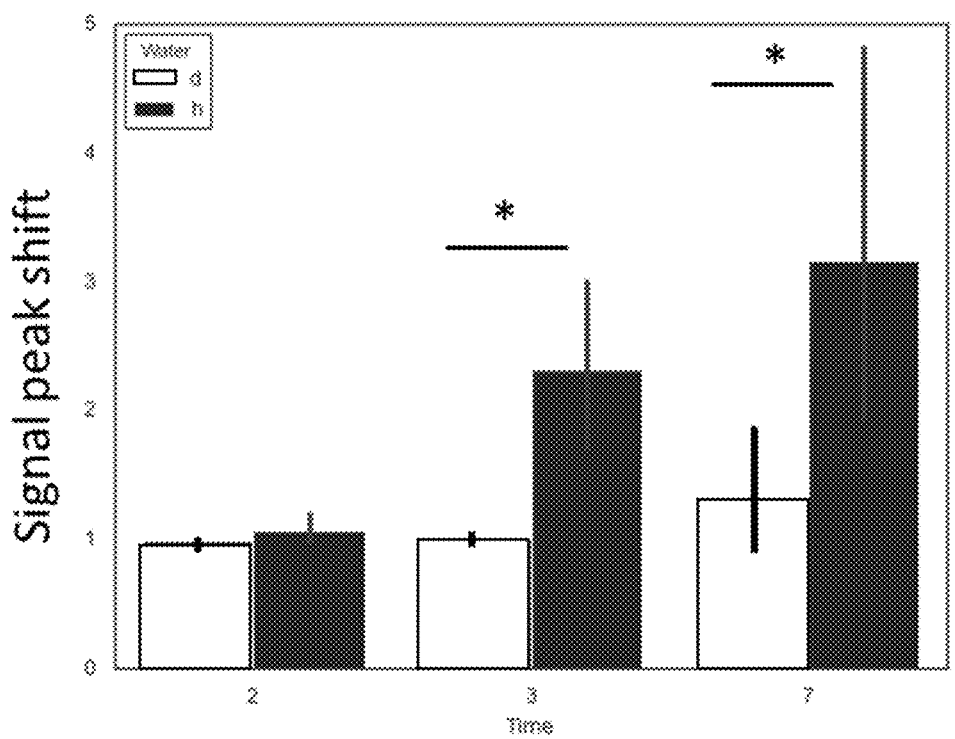

The data represented in FIGS. 4A and 4B implies a significant, potent solvent effect of $D_2O$ on the mRNA stabilization at 3 and 7 days of incubation at 37° C. FIG. 4A demonstrates a significantly higher degree of mRNA preservation (p<0.0001;

Two-way ANOVA followed by Tukey test for multiple comparisons; solvent by time interaction p<0.001, Two-way ANOVA) and FIG. 4B confirms that the template-specific maximum signal shifts significantly only when $H_2O$ was used as a solvent (p<0.05; Two-way ANOVA and Tukey correction for multiple comparisons).

The experiments in this example demonstrated a great increase of mRNA stability if mRNA was produced and stored in deuterium oxide, over the period of 2 days, 3 days, and 7 days exposure to 37° C. Messenger RNA molecules the were produced and stored in the deuterium oxide showed more than 80% preservation during 7 days storage at 37° C. Production and storage of mRNA in deuterium oxide increased its s stability more than 10 fold during the 7 day incubation at 37° C.

Without wishing to be bound by theory, we propose the explanation whereby mRNA forms tighter secondary structure in $D_2O$ protecting 2' hydroxyl on the ribose from participating in nucleophilic attack on the phosphodiester bond. This effect may at least in part be due to the smaller size of $D_2O$ in comparison with $H_2O$ and due to the weaker intermolecular bonds in $D_2O$ in comparison to $H_2O$.

Example 2: Isotope Kinetic Effect Resulting from mRNA Synthesis with Deuterated Nucleotides This example aimed to understand the contribution of isotope kinetic effect on mRNA stabilization from the quantified data by comparing the mRNA preservation between groups of different nucleotides used in the IVT. The isotopic kinetic effect is referred to when the variance in the data is driven by protium to deuterium substitution in the molecule of interest.

Figure 5:
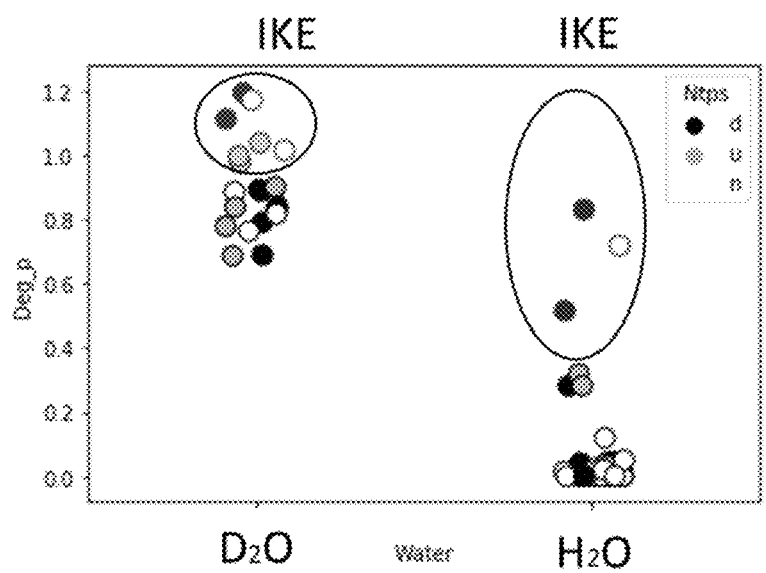
FIG. 5 is a dot graph depicting isotope kinetic effect in mRNA stability over time in $H_2O$ and $D_2O$, in accordance with the Examples described herein.
Figure 6:
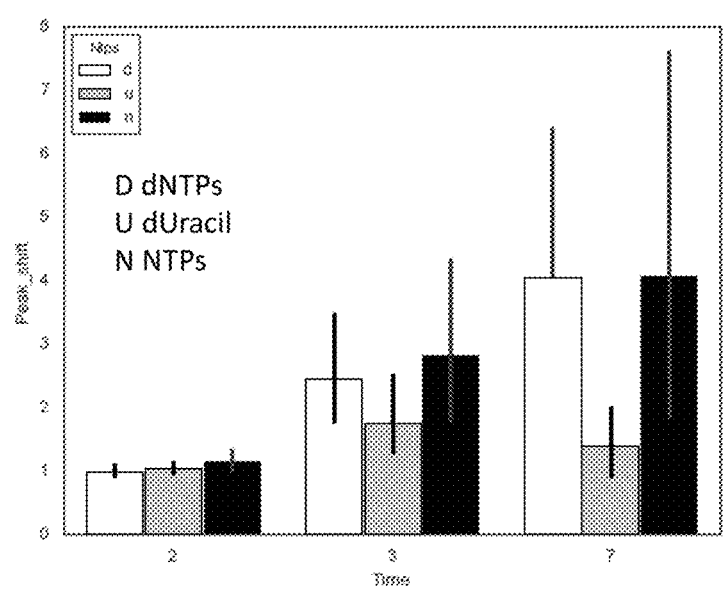
FIG. 6 is a bar graph depicting isotope kinetic effect in mRNA stability over time in $H_2O$ and $D_2O$, in accordance with the Examples described herein.

In this study, rNTPs with various extent of deuteration (Table 1) were used to introduce deuterium atoms into mRNA molecules. The IVTs were conducted with these rNTPs in $H_2O$ or $D_2O$. The isotope kinetic effect is referred to when the variance in the data is driven by protium to deuterium substitution in the molecule of interest. The isotope kinetic effect was masked in the deuterated environment (FIG. 5, $D_2O$ group) but was visible when mRNA was synthesized and stored in $H_2O$ (FIG. 5, $H_2O$). The stabilizing effect of deuterated Uracil became apparent at 3 days of 37° C. exposure and reached statistical significance at one week (FIG. 6, p<0.05, 2-way ANOVA followed by Tukey test for multiple comparisons).

Figure 7A:
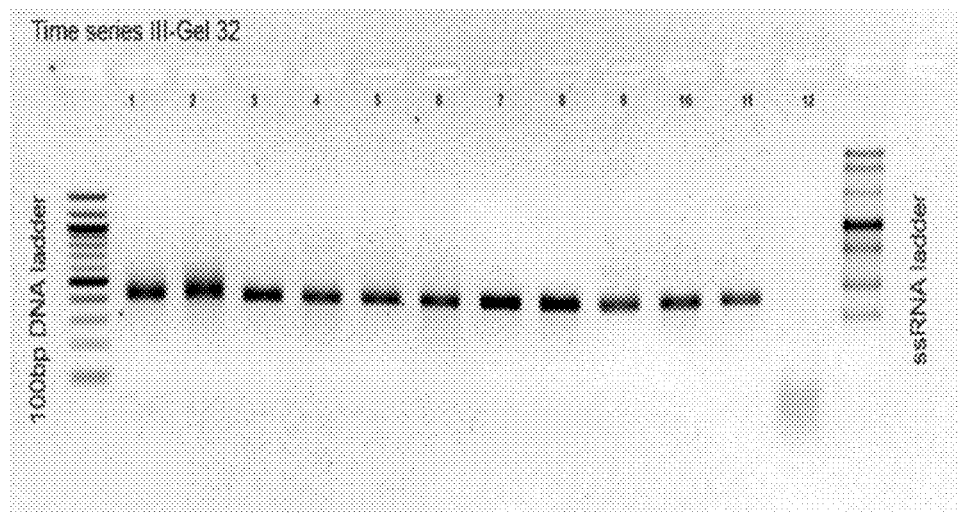
FIGS. 7A and 7B are pictures of an agarose gel showing electrophoresis of mRNA produced and stored in $D_2O$ (FIG. 7A) or stored in $H_2O$ (FIG. 7B) and subjected to 37° C. for 2 days, in accordance with the Examples described herein. Description of the lanes in found in Table 1 hereinafter.
Figure 7B:
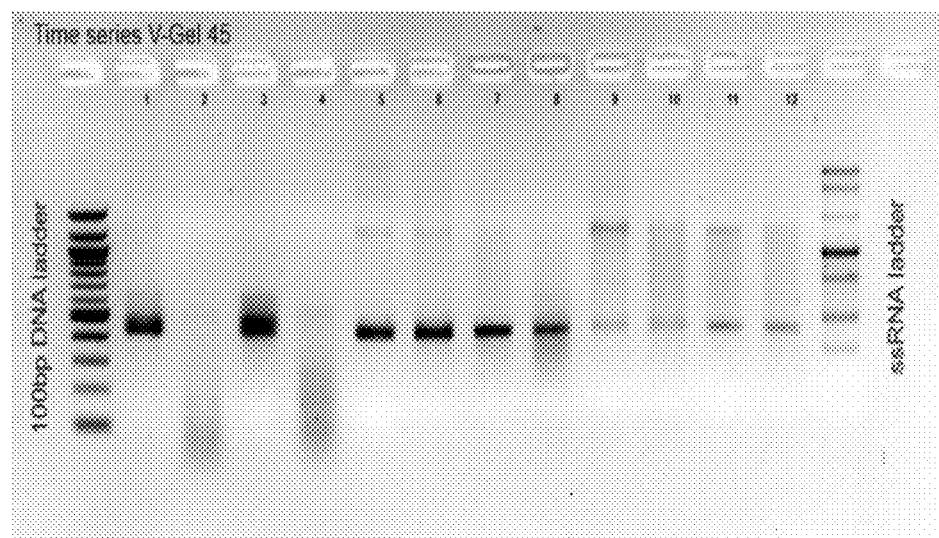

Until this point in the study, mRNA was either made and stored in $H_2O$ or made and stored in $D_2O$. The importance of mRNA synthesis in $D_2O$ alone was not addressed. To address the effect of mRNA synthesis in $D_2O$ on mRNA stability, IVT was performed either in $H_2O$ followed by storage of mRNA in $D_2O$ or in $D_2O$ and stored in $H_2O$ and the mRNA stability was assessed by thermal hydrolysis experiments. FIGS. 7A and 7B show representative agarose gels of the experiment. mRNA synthesized and stored in $D_2O$ was resistant to thermal hydrolysis after 3 days of the exposure to 37° C. regardless of the template GC content or rNTPs deuteration (FIG. 7A). However, if mRNA was produced in $H_2O$, the stabilization effect of $D_2O$ was greatly reduced (FIG. 7B).

Figure 8A:
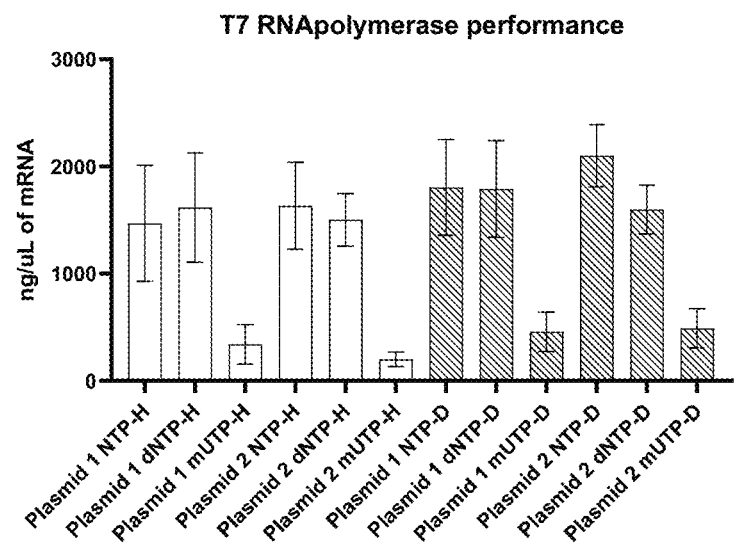
FIG. 8A is a bar graph depicting the effect of $D_2O$ on the efficacy of T7 RNA polymerase, in accordance with the examples. White bars represent mRNA synthesis is in $H_2O$ and grey bars represent mRNA synthesis in $D_2O$.
Figure 8B:
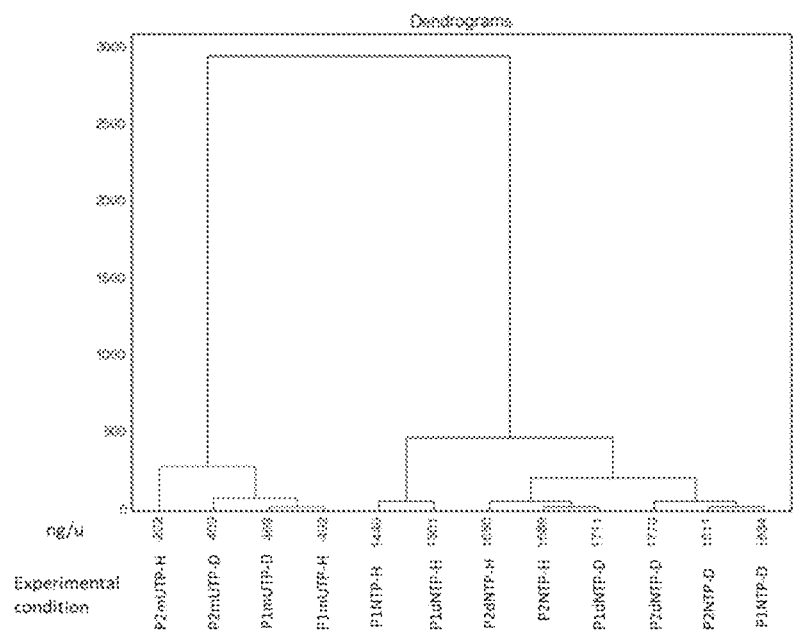
FIG. 8B is a graph showing hierarchical clustering of 12 experimental conditions, in which the performance of T7 RNA polymerase was assessed, in accordance with the Examples described herein.

To elucidate the mechanism of mRNA stabilization during IVT, the performance of T7 RNA pol was assayed. As shown in FIG. 8A, using fully deuterated environment for mRNA synthesis reduced the extent of mRNA degradation during IVT process. There were no statistical differences between the mRNA quantities produced in $D_2O$ and $H_2O$ (One-way ANOVA, p<0.05).

We performed hierarchical clustering of the 12 conditions (FIG. 8A). The $H_2O$ and $D_2O$ experimental conditions clustered together The condition that clustered away from all others were when mUTPs were used and the concentration of mRNA was reduced $H_2O$ and $D_2O$ conditioned clustered together as well.

Figure 9:
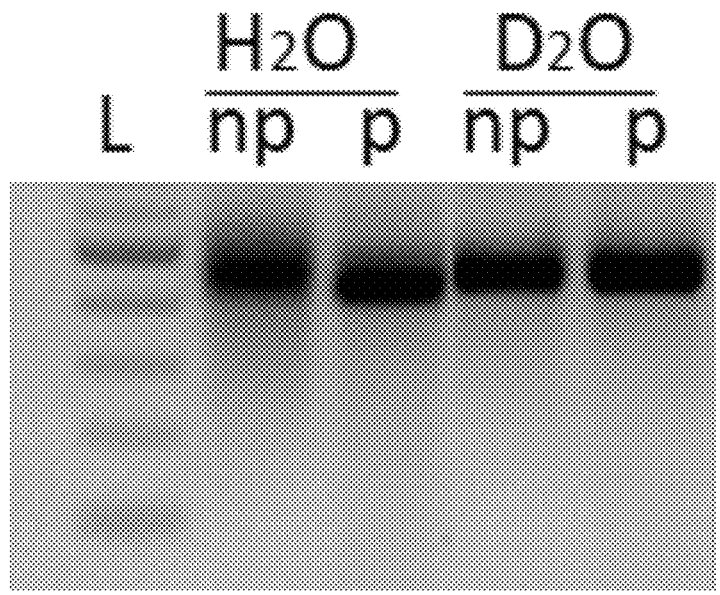
FIG. 9 is a picture of an agarose gel electrophoresis of purified and non-purified mRNAs produced in $H_2O$ and $D_2O$ showing increase of mRNA stabilisation during synthesis in $D_2O$, in accordance with the Examples described herein. Gel lanes are labelled as follows: mRNA synthesized with T7 RNA Pol (T7) in $H_2O$ (H) or $D_2O$ (D), and the mRNA was either purified (p) or left non-purified (np).

To explore further the stabilizing effect of mRNA synthesis in $D_2O$, the IVTs were conducted in $H_2O$ and $D_2O$ and the results were compared before and after on-column purification of the RNA products. We hypothesized that on-column purification could potentially mask the true occurrence of high and low molecular size impurities during IVT. The IVT was performed in $H_2O$ and $D_2O$ at 37° C., which is a temperature supportive of thermal hydrolysis. FIG. 9 shows a representative agarose gel electrophoresis of purified and non-purified mRNAs produced in $H_2O$ and $D_2O$. mRNA synthesized in $D_2O$ showed increased stability during IVT. The specific signal bands are sharper and more "crisp" when mRNA was produced in $D_2O$ regardless of the purification status of the sample. This supports the present invention in the fact that synthesis of mRNA in $D_2O$ reduces the degradation already during the IVT proper, as evidenced by a decreased signal from small fragments in the degradation zone (area below the specific signal).

In summary, this study used two types of deuterated rNTPs to synthase mRNA: deuterated uracil with other RNTPs not changed and a mix of deuterated RNTPs. The stabilization effect was observed in $H_2O$ more readily than in $D_2O$. Without wishing to be bound by any theory, we speculate that because the preservation of mRNA in the $D_2O$ was already between 80% and 90% the effect of substitution of non-deuterated RNTPs with the deuterated ones could be masked. In contrast, in $H_2O$, where the preservation was lower the effect of deuteration of the RNTPs was statistically significant improvement of mRNA stability.

Figure 10:
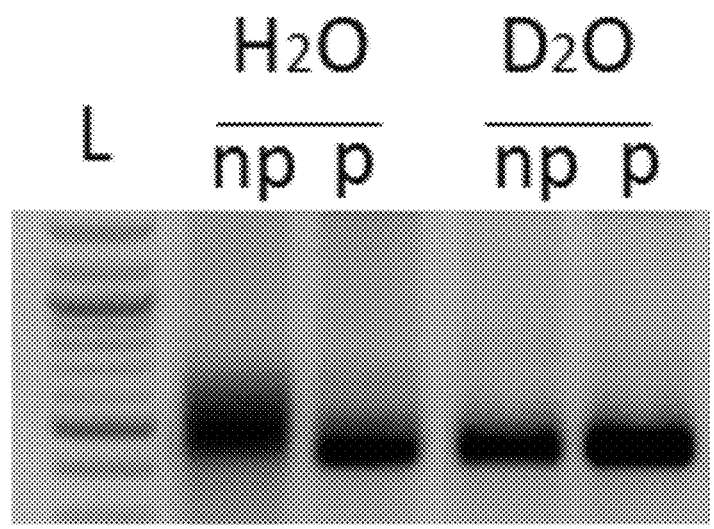
FIG. 10 is a picture of an agarose gel electrophoresis of purified and non-purified mRNAs showing that synthesis of mRNA in $D_2O$ reduces the contamination of mRNA with large size fragments, in accordance with the Examples described herein. Gel lanes are labelled as follows: mRNA synthesized with T7 RNA Pol (T7) in $H_2O$ (H) or $D_2O$ (D), and the mRNA was either purified (p) or left non-purified (np).

Example 3: Synthesis of mRNA in $D_2O$ Reduces the Contamination of mRNA with Large Size Fragments We demonstrated in FIG. 8A that T7 RNA Pol performs at least as well in $D_2O$ as in $H_2O$. We next studied whether synthesis of mRNA in $D_2O$ could reduce the contamination of mRNA with large size fragments. mRNAs were synthesized as described and purified (p) as described in Materials and Methods or left unpurified (np). As shown in FIG. 10, there was less signal intensity observed in the higher molecular weight area in mRNA synthesized in $D_2O$.

Figure 11A:
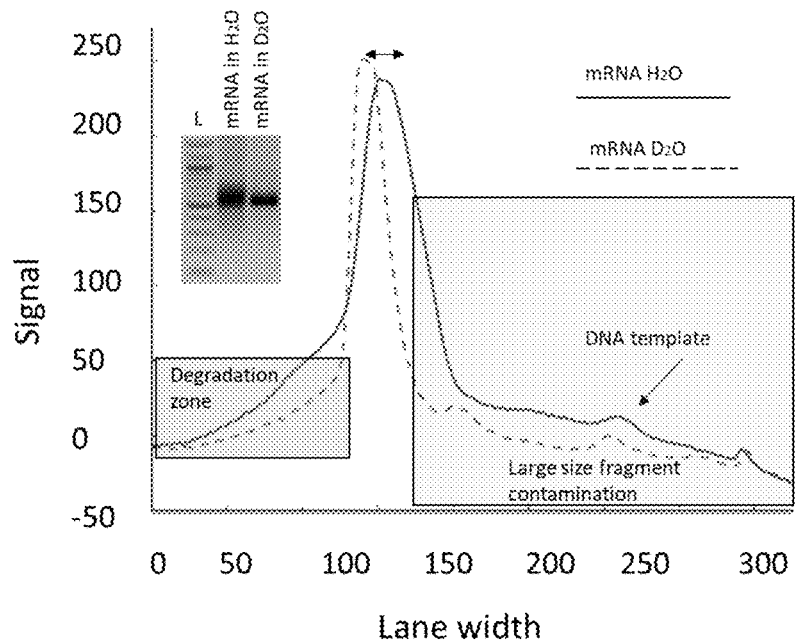
FIGS. 11A and 11B are graphs showing distribution curves used for assessing non-purified mRNA integrity during synthesis in $H_2O$ and $D_2O$ (FIG. 11A) or during synthesis in $D_2O$ (FIG. 11B), in accordance with the Examples described herein.
Figure 11B:
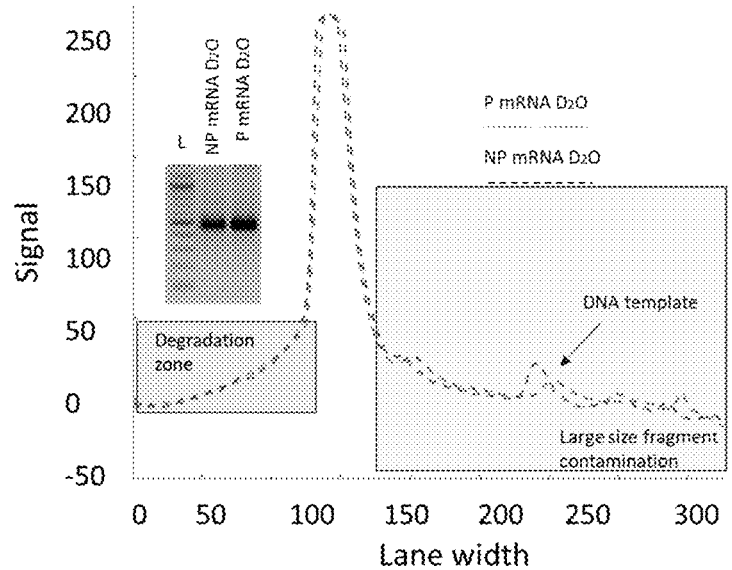
Figure 12A:
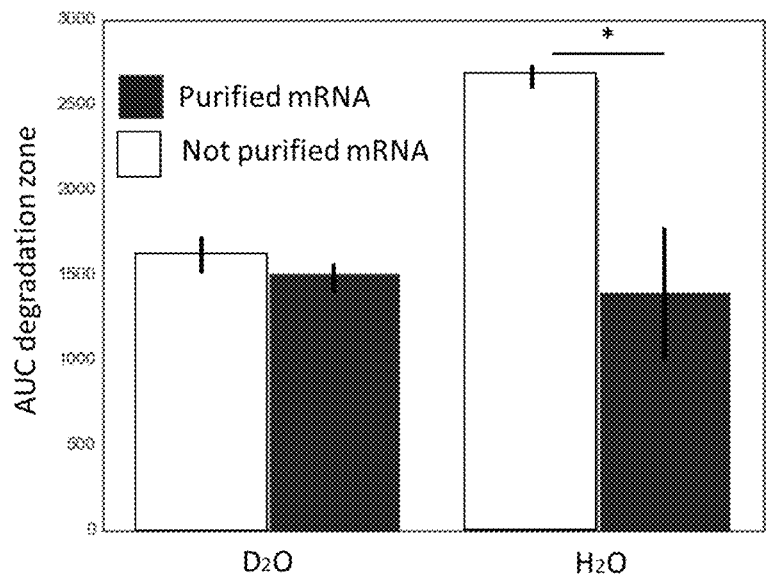
FIG. 12A is a bar graph depicting statistical analysis of the degradation zone in purified and non-purified mRNA produced in $H_2O$ and $D_2O$, in accordance with the Examples described herein.

The signal quantification and comparison of non-purified products are described in FIGS. 11A-B and 12A-B. mRNA was subject to more degradation during the IVT in $H_2O$ than in $D_2O$, as indicated by the higher signal arising from the degradation zone (FIGS. 11A, 12A). Also, post-IVT purification significantly (p<0.0001, Two-way ANOVA followed by Tukey correction) reduced the degradation zone signal in the mRNA synthesized in $H_2O$ (FIG. 12A) but had no effect on the quality of mRNA produced in D$_2$O (FIGS. 11B, 12A). The pre-purification quality of mRNA synthesized in D$_2$O was comparable to purified mRNA synthesized in H$_2$O (FIG. 12).

Figure 12B:
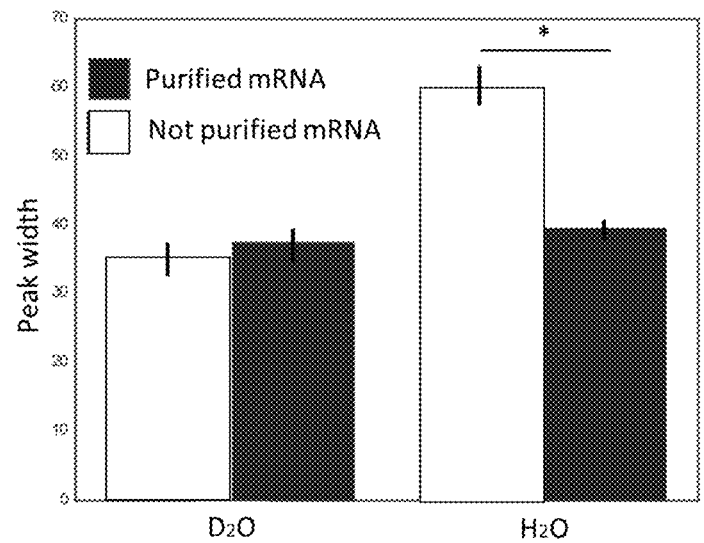
FIG. 12B is a bar graph depicting statistical analysis of a large molecular fragment contamination zone in purified and non-purified mRNA produced in $H_2O$ and $D_2O$, in accordance with the Examples described herein. The width of the specific signal peak at 850 bp was used as a proxy for T7 RNA Pol specificity.

The width of the specific signal peak at 850 by was used as a proxy for T7 RNA Pol specificity. The narrower the peak, the lesser the spread of molecular weight around the expected band at 850 bp. A wide peak indicates occurrence of arbitrary elongation and degradation products. Post IVT purification significantly (p<0.001, Two-way ANOVA followed by Tukey test) reduced the peak width of mRNA produced in H$_2$O (FIG. 12B). There was no statistically significant difference between purified and non-purified mRNA produced in D$_2$O (FIGS. 11B, 12B). Generally, mRNA synthesized in D$_2$O demonstrated a more compact size distribution and the bulk signal appeared at a slightly lower molecular weight (FIG. 11A, double arrow; FIG. 12B), likely due to a tighter secondary structure of mRNA forming in D$_2$O. It is possible that fewer large molecular weight contaminants occur during IVT in D$_2$O due to constrains that D$_2$O imposes on mRNA structure and T7 RNA Pol folding. Curiously, the IVT with T7 in D$_2$O also seems to be more efficient since it produced more of the specific 850 bp mRNA with less template (blue arrow in FIG. 11A).

Therefore, there is less degradation and high molecular weight artifacts in non-purified mRNA synthesized in D$_2$O than in H$_2$O (FIG. 11A). Also, there is no significant effect of post IVT purification on the degradation zone signal and high molecular weight contamination in mRNA synthesized in D$_2$O as evidenced by the overlapping signal curves of purified and non-purified mRNA (FIG. 11B). D$_2$O improves mRNA stability and reduces contamination with large molecular weight mRNA products during IVT.

The results in differences in mRNA integrity after synthesis in H$_2$O or D$_2$O are also very persuasive. mRNA showed more degradation during the IVT in H$_2$O than in D$_2$O as was shown by the larger degradation zone (FIG. 12A). Purification significantly reduced the degradation zone signal in mRNA synthesized in H$_2$O but not in D$_2$O (Two-way ANOVA followed by Tukey correction p<0.0001).

As shown in FIG. 12B, post IVT purification significantly reduced the peak width in mRNA produced in light water, but no statistically significant change was observed between purified and non-purified mRNA produced in D$_2$O (Two-way ANOVA followed by Tukey correction p<0.001).

Figure 13A:
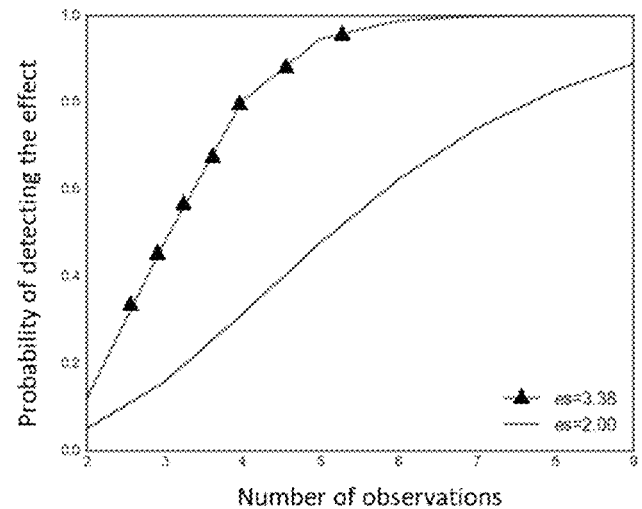
FIG. 13A is a line graph depicting power analysis of the degradation zone statistics, in accordance with the Examples described herein.
Figure 13B:
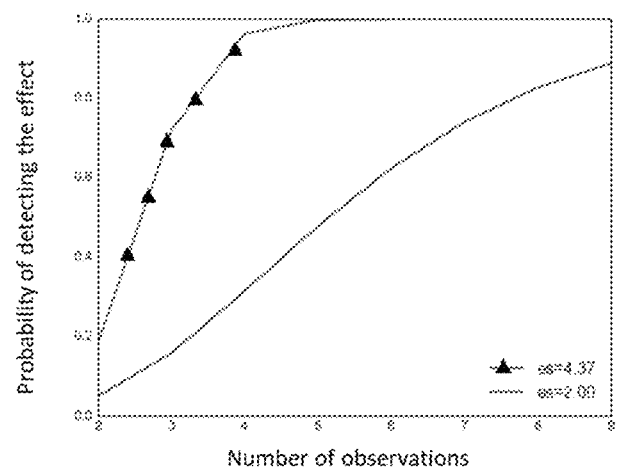
FIG. 13B is a line graph depicting power analysis of large molecular weight contamination zone statistics, in accordance with the Examples described herein.

Statistical power analysis of mRNA synthesis in H$_2$O and D$_2$O experimental data. Power analysis only considers scenario when true null hypothesis is correctly rejected (true positive). It calculates the probability of finding the difference when there is a difference between means of two populations. High probability from 0.8 to 1 suggest the ability of detection of true difference. Statistical power depends on effect size, variability of the data that depends on the number of observations, and confidence/significance value $\alpha$. Value $\alpha$ defined by the research as a cut of desirable statistical significance. The most widely accepted level of statistical significance accepted in the peer review scientific publication and the court of law of majority of the countries including USA and Canada is 0.05. In FIG. 13A the line with the triangle symbols depicts the increase in statistical power (y axis) as the sample size increases (Number of Observations, x axis) at significance level $\alpha$=0.05 and the effect size of the degradation zone (AUC) is 3.38. With this effect size the power at n=3 is higher than 0.8 The line without symbol is given as an example of an effect size of 2. The steeper the curve the smaller number of observations is required to achieve a high power. In FIG. 13B the line with the triangle symbols depicts the increase in statistical power (y axis) as the sample size increases (Number of Observations, x axis) at significance level $\alpha$=0.01 and the effect size of signal spread is 4.37. With this effect size the power at n=3 is higher than 0.9. The line without symbol is given as an example of an effect size of 2. The power analysis suggests that with such prominent effect sizes 3 observations are sufficient to demonstrate significant differences between the groups.

Therefore, given the pilot data, power analysis gives information about the number of samples required to demonstrate statistically (at the level $\alpha$) significant differences between means of two population. Also, power analysis provides the information about statistical power in existing data.

Power analysis is advantageous in that it provides information about magnitude of the experimental effect and required sample size, while strict testing of null hypothesis using the threshold p value provides binary output: reject or accept.

Figure 20:
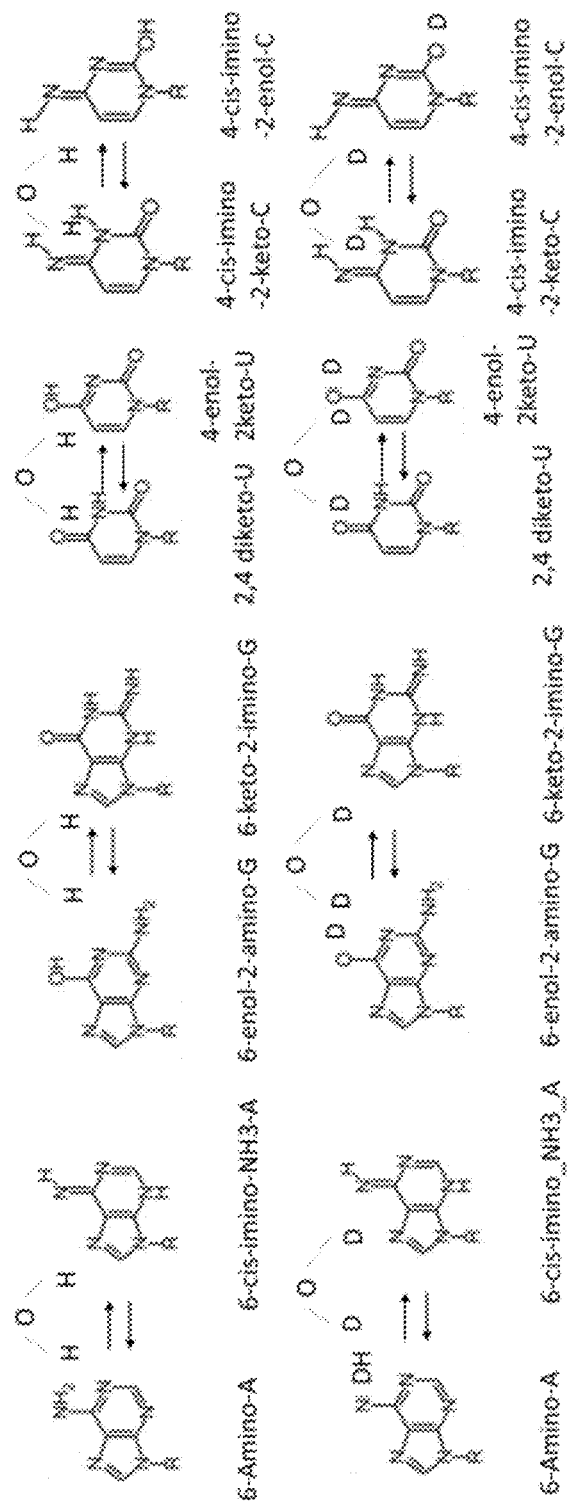
FIG. 20 is a diagram illustrating selected examples of deuterium incorporation into mRNA molecules during mRNA synthesis via keto-enol tautomerization mechanism.

As is known, during manufacturing the yields of mRNA are significantly reduced during the IVT process. The present examples demonstrate that conducting mRNA synthesis in D$_2$O and storing mRNA in D$_2$O improved the mRNA stability in two aspects. Firstly, mRNA showed less degradation during the IVT process. This could potentially lead to better economic characteristics of the production process. Second, the contamination with large molecular-weight fragments was reduced when mRNA was made in D$_2$O. This could also increase the efficiency of mRNA synthesis. Without wishing to be bound by any theory, we propose that during mRNA synthesis, due to tautomerism, Deuterium incorporates into mRNA backbone enhancing it's stability and resistance to thermal and enzymatic hydrolysis. In this regard, FIG. 20 depicts non-exhaustive examples of deuterium incorporation into mRNA molecules during mRNA synthesis via keto-enol tautomerization.

Example 4: Effect of mRNA Secondary Structure and/or GC Content on Stabilization by D$_2$O This experiment was designed to explore the stabilizing effect of D$_2$O on mRNA by focusing on analyzing the contribution of mRNA secondary structure to the phenomenon. This was done using template plasmid P1 (here "a") which has 38.8% GC content and MFE of −141.30 kcal/mol (less structured and stable secondary structure), whereas template plasmid P2 (here "g") has 63.2% GC content with a MFE of −256.30 (more structured and stable secondary structure).

The mRNA was synthesized using both templates in H$_2$O and D$_2$O and subjected to high temperature treatment. The treatment paradigms included a challenge in 45° C. (non-denaturing condition at which the mRNA secondary structure is believed to be preserved) and a challenge in 65° C. (denaturing condition at which the secondary structure of mRNA ceases to exist). These approaches were designed to assay the effect of D$_2$O stabilization on the mRNA with differing GC content and secondary structures.

Figure 14A:
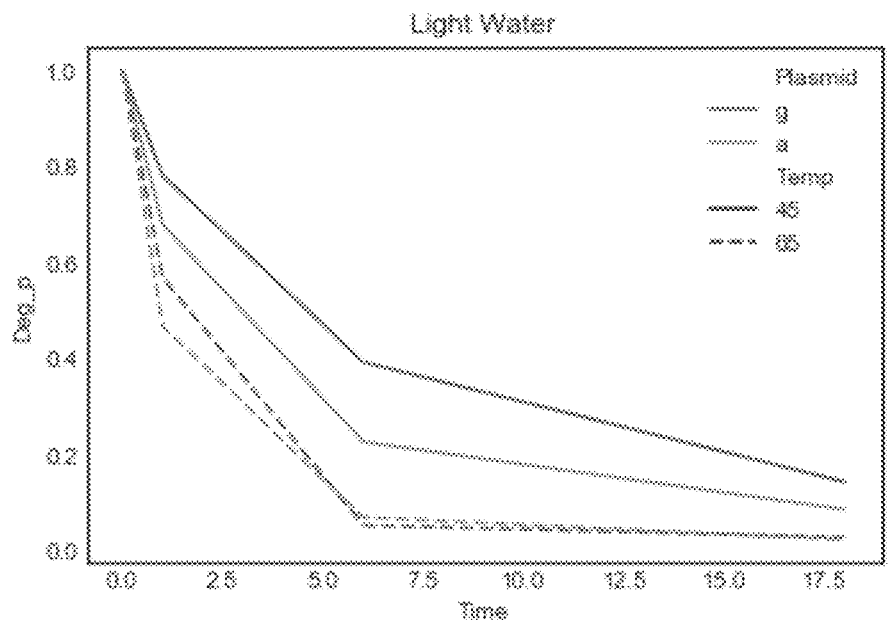
FIGS. 14A and 14B are line graphs depicting the effect of secondary structure on mRNA stability in $H_2O$ (FIG. 14A) or in $D_2O$ (FIG. 14B), in accordance with the Examples described herein.
Figure 14B:
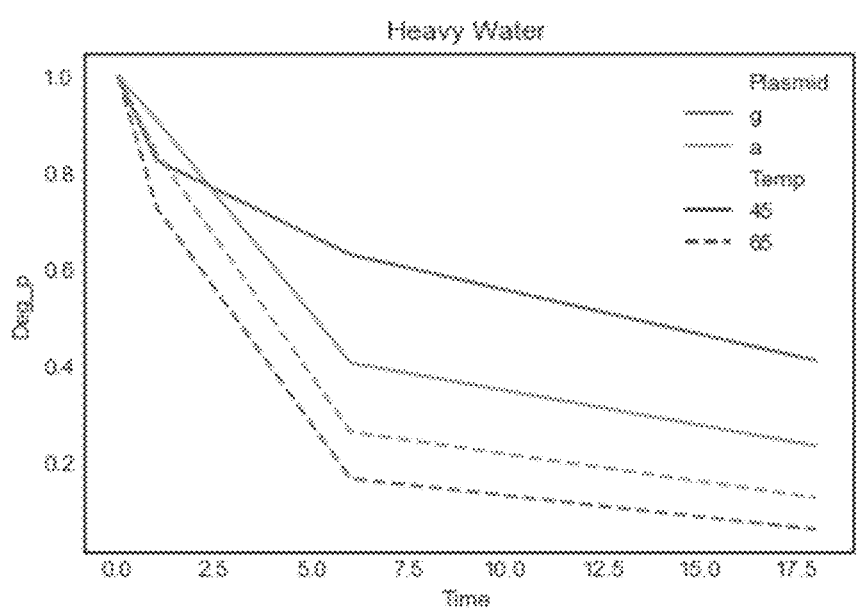

As expected, in H$_2$O the GC rich mRNA showed the highest stability at 45° C., measured as degree of preservation (FIG. 14A). This phenomenon disappeared at 65° C., when secondary structure no longer protects against denaturation. In D$_2$O, the GC-rich template again demonstrated the best stability, but stability of the GC-poor mRNA was greatly improved to the level of the GC-rich template in H₂O. In H₂O the GC-rich mRNA showed the highest stability at 45° C., likely owing to the more stable secondary structure. This effect disappeared at 65° C. when the secondary structure is no longer protective of denaturation (FIG. 14B).

Without wishing to be bound by theory, this could be in part due to a more compact mRNA structure in D₂O. In D₂O, both mRNA templates were stabilized at 45° C., and to a lesser degree even at 65° C., at every time point as evidenced by higher degrees of preservation than in H₂O (FIG. 14A). At 45° C. and in D₂O the GC-rich mRNA showed the best stability. The GC-poor template was stabilized at 45° C. in D₂O close to the degree of GC-rich template at 45° C. in H₂O.

Example 5: In Vitro Translation Capacity of mRNA Synthesized in D₂O

Figure 15A:
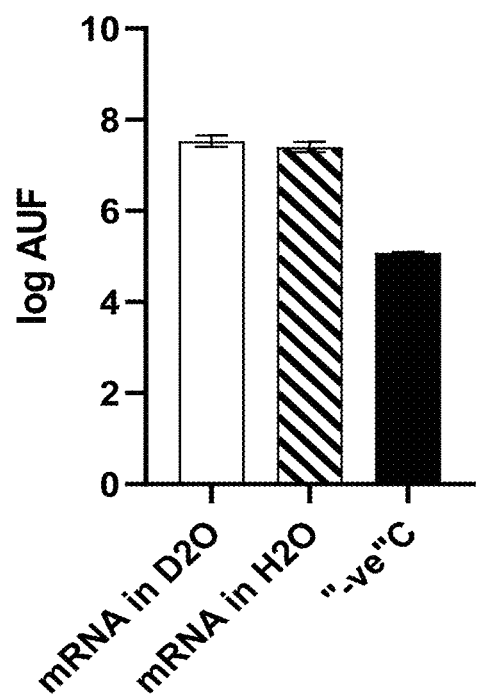
FIG. 15A is a bar graph depicting fluorescence analysis of translation of mRNA synthesised and stored in $D_2O$ into functional protein, in accordance with the Examples described herein.
Figure 15B:
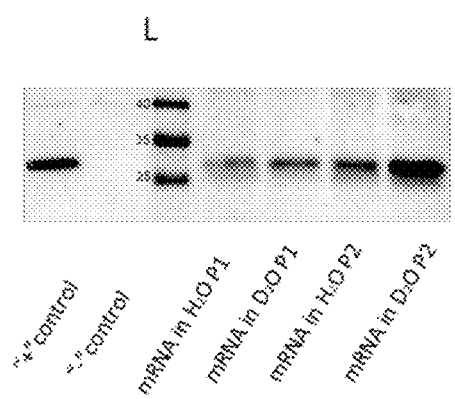
FIG. 15B is a picture of a western blot analysis depicting translation of mRNA synthesised and stored in $D_2O$ into functional protein, in accordance with the Examples described herein.

To be a viable option for stabilization of mRNA in synthesis and storage, D₂O should not interfere with the translation of the mRNA template into protein. This was tested by comparing the in vitro translation of P1 GFP mRNA synthesized and stored in D₂O or H₂O (FIGS. 15A and 15B).

The amount of translated GFP directly contributes to the intensity of the fluorescence signal in the sample. The emission intensities were log-transformed for normalization. There was no statistically significant difference between the GFP fluorescence intensities in translation products of mRNA templates produced and stored in H₂O or D₂O (one-way ANOVA with Bonferroni correction for multiple comparisons, $p>0.05$). Therefore, we conclude that mRNA produced and stored in D₂O can be translated into a functional protein (FIG. 15A).

The protein samples were resolved on the polyacrylamide gel and transferred to PVDF membrane (Material and Methods). The membrane was probed with anti-GFP antibody as described in the Western blot section of materials and methods. In all instances 1 ug of mRNA was used for the in vitro translation experiments. The efficiency of the in vitro translation of mRNA prepared and stored in D₂O was at least as good as of mRNA prepared in the H₂O (FIG. 15B).

Example 6: In Vivo Translation Capacity of mRNA Synthesized in D₂O

Figure 16A:
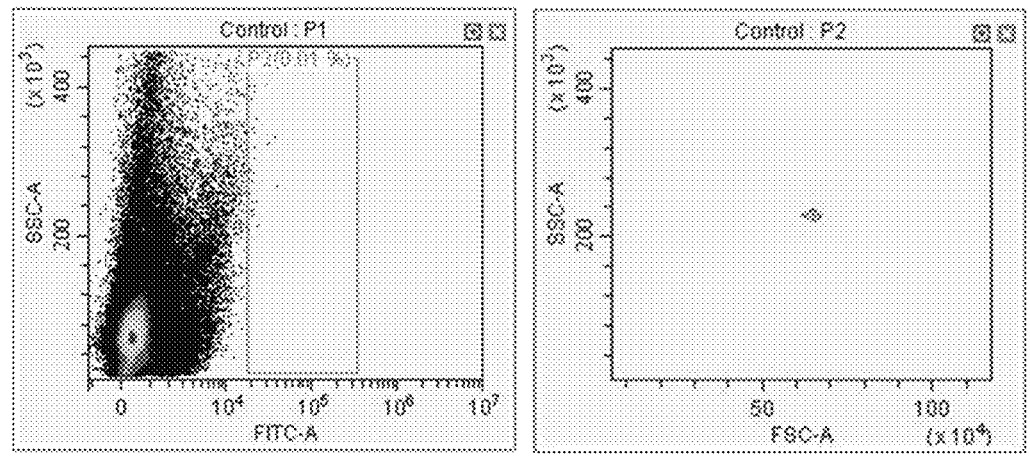
FIGS. 16A and 16B are graphs showing flow cytometry analysis of murine splenocyte after control injection (FIG. 16A) or after injection with mRNA produced and stored in $D_2O$ (FIG. 16A), in accordance with the Examples described herein.
Figure 16B:
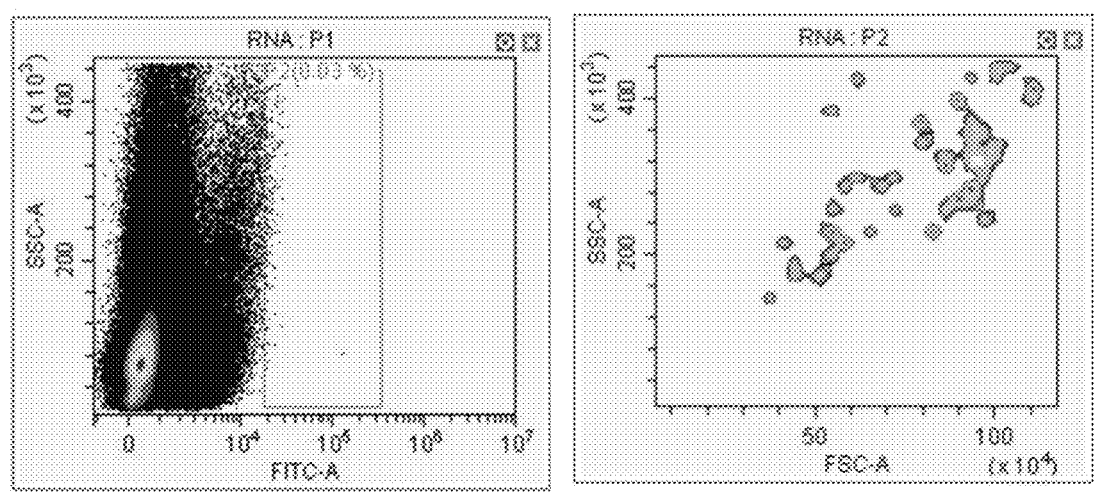

Flow cytometry analysis of GFP expression in mouse splenocytes after an intraperitoneal injection of mRNA synthesized and stored in D₂O is shown on the FIG. 16. It was confirmed that the injected mRNA had resulted in the translation of the coded protein GFP. Furthermore, although not labeled with specific markers, the side scatter (SSC, y-axis) and forward scatter (FSC, x-axis) metrics of GFP signal suggest that the majority of GFP positive cells belong to a subset of dendritic cells. Other cell types that express GFP potentially include activated macrophages and neutrophils. To further phenotype GFP positive cells markers such as CD11c, CD11b, MHCII, CD80, CD86, Ly6C, Ly6G can be used.

Figure 17A:
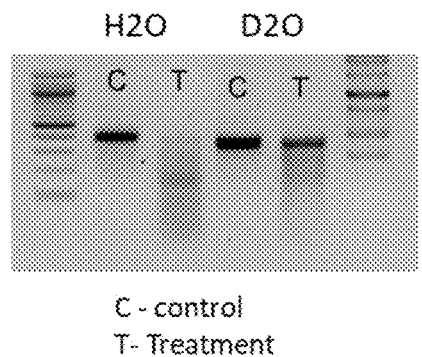
FIGS. 17A, 17B and 17C are panels with pictures of a gel depicting enzymatic degradation of mRNA synthesized and stored in either $D_2O$ or $H_2O$, and concentration of RNAse A dependent effect on mRNA preservation when it is synthesised and stored in $H_2O$ or $D_2O$, in accordance with the Examples described herein.
Figure 17B:
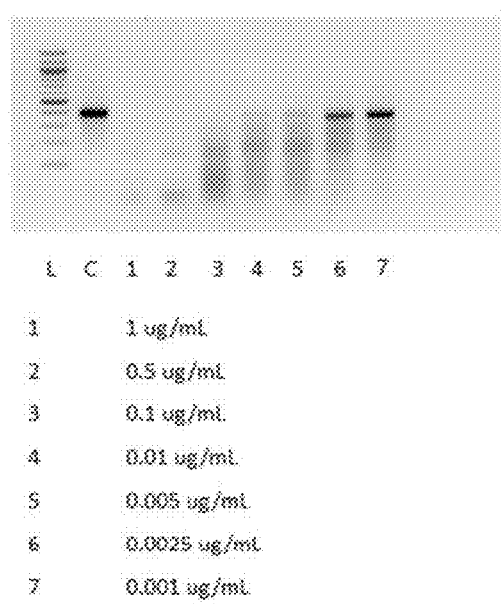
Figure 17C:
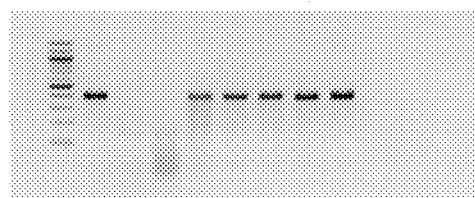

Example 7: Synthesis and Storage of mRNA in D₂O Protects it from Enzymatic Hydrolysis As is known, RNAse A catalyzes mRNA hydrolysis. In this study 0.01 µg of RNAse A was used to treat 500 ng on mRNA. The mRNA then was resolved on the agarose gel and the data were acquired with Image J™. As shown in in FIG. 17A, The degradation of mRNA was much less pronounced in mRNA that was synthesized and stored in D₂O than in mRNA that was produced and stored in H₂O. FIGS. 17B and 17C demonstrate concentration dependent hydrolysis by RNAse A of mRNA produced and stored in H₂O and D₂O. mRNA produced and stored in D₂O demonstrated stronger resistance to RNAse mediated hydrolysis in concentration dependent manner.

Example 8: Isolation and Characterization of Total RNA from Murine Primary Splenocytes Total RNA stabilization as well as in vitro RNA transcription protocol was tested. Total RNA was extracted and the RNA was eluted into 100 µL of D₂O or 100 uL of H₂O and quantified using Nanodrop™ spectrophotometer. The experiments were designed to test the hypothesis that replacing U with dU increases mRNAnlrx1 stability, is synthesized de novo using T7 or SP6 RNA polymerases from existing plasmids using commercially available kits (Promega #E2040S HI Scribe. The Uridine in the RNA synthesis was replaced with Uridine-D13 (Sigma 902454-1MG). RNA aliquots of 30 µL (100 ng) were used for temperature degradation tests. RNA aliquots were subjected to different temperature treatments for different incubation times: 65° C., 37° C. or room temperature (RT) for 10, 60 min and 12 hours. This incubation was performed in a thermocycler to avoid evaporation as previously described. Alternatively, RNAase A treatment was used to cleaves the 3'-end of unpaired C and U residues. The RNA was resolved on 1% agarose gel and stained with EtBr for visualization. The data was analyzed using a gel imaging system and image J™ software. The samples we also tested using Agilent Bioanalyzer 2100™ and RNA integrity numbers will be obtained.

Figure 19:
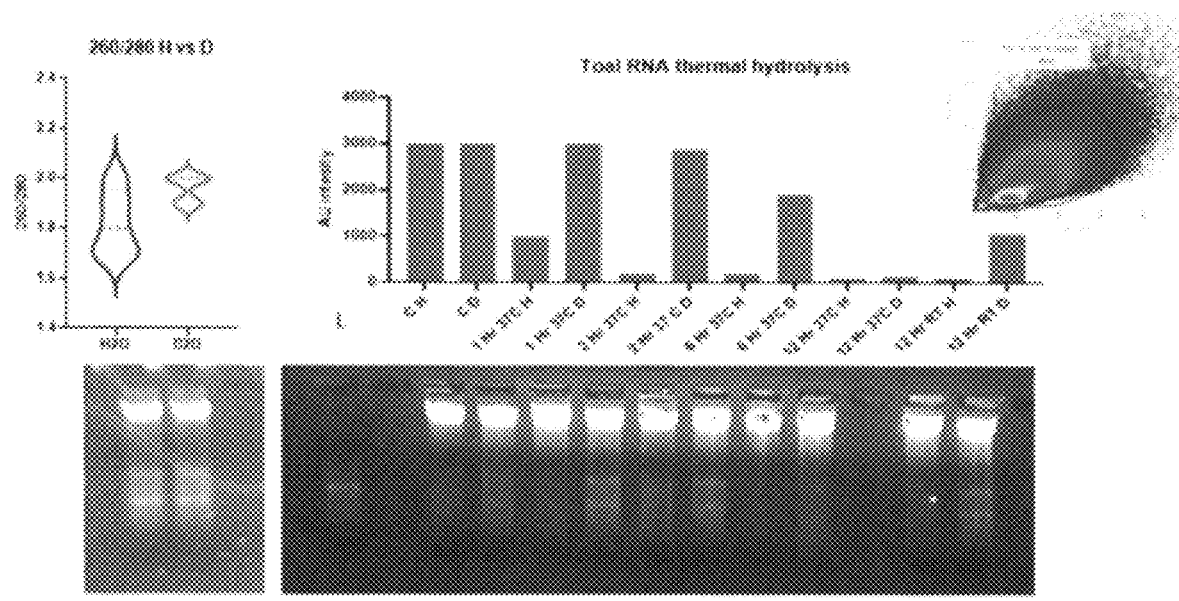
FIG. 19 is a panel showing isolation and characterization of total RNA from murine primary splenocytes.

As shown in FIG. 19, resuspension of total RNA in D₂O resulted in increased RNA stability at 37 degrees Celsius.

Headings are included herein for reference and to aid in locating certain sections. These headings are not intended to limit the scope of the concepts described therein, and these concepts may have applicability in other sections throughout the entire specification. Thus, the present invention is not intended to be limited to the embodiments shown herein but is to be accorded the widest scope consistent with the principles and novel features disclosed herein.

As used herein, the terms, "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

The singular forms "a", "an" and "the" include corresponding plural references unless the context clearly dictates otherwise. Thus, for example, reference to "a RNA molecule" includes one or more of such molecules and reference to "the method" includes reference to equivalent steps and methods known to those of ordinary skill in the art that could be modified or substituted for the methods described herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contains certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. An aqueous composition comprising deuterium-stabilised messenger RNA (mRNA) molecules that have been synthesised in the presence of deuterium.

2. The aqueous composition of claim 1, wherein said deuterium is present at a concentration of at least 85 atom % D.

3. The aqueous composition of claim 1, wherein said deuterium is present at a concentration of about 85 atom % D to about 99.9 atom % D.

4. The aqueous composition of claim 1, wherein said deuterium-stabilised mRNA molecules incorporates deuterium.

5. The aqueous composition of claim 4, wherein said deuterium-stabilised mRNA molecules comprise deuterated ribonucleosides.

6. The aqueous composition of claim 4, wherein said deuterium-stabilised mRNA molecules comprise substitution of protium atoms by deuterium atoms.

7. The aqueous composition of claim 4, wherein said deuterium-stabilised mRNA molecules comprise a deuterium atom in the 2'OH-group on the ribose sugar moiety.

8. The aqueous composition of claim 1, wherein said stabilised deuterium-stabilised mRNA molecules display at least one of: i) increased structural integrity of their primary and/or secondary structure, compared to non-stabilized mRNA molecules; and ii) increased resistance to degradation compared to non-stabilised mRNA molecules.

9. The aqueous composition of claim 1, wherein said deuterium-stabilised mRNA molecules display increased resistance to at least one of (i) hydrolysis or degradation by endonucleases, and (ii) thermal degradation.

10. The aqueous composition of claim 1, wherein said deuterium-stabilised mRNA molecules display increased resistance to thermal hydrolysis after 1 day of exposure to 37° C.

11. The aqueous composition of claim 1, wherein said deuterium-stabilised mRNA molecules display increased resistance to thermal hydrolysis after a challenge at 45° C.

12. The aqueous composition of claim 1, wherein said aqueous composition further comprises deuterium in solution.

13. The aqueous composition of claim 1, wherein said deuterium-stabilised mRNA molecules are components of a vaccine.

14. An aqueous messenger ribonucleic acid (mRNA) composition comprising (i.) an aqueous solution comprising deuterium at a concentration sufficient for stabilising mRNA molecules; and
(ii) deuterium-stabilised mRNA molecules that have been synthesised in the presence of deuterium.

15. The aqueous mRNA composition of claim 14, wherein the aqueous solution comprises a deuterium concentration of at least 85 atom % D.

16. The aqueous mRNA composition of claim 14, wherein the aqueous solution comprises deuterium at a concentration of about 85 atom % D to about 99.9 atom % D.

17. The aqueous mRNA composition of claim 14, wherein said deuterium-stabilised mRNA molecules incorporates deuterium.

18. The aqueous mRNA composition of claim 17, wherein said deuterium-stabilised mRNA molecules comprise deuterated ribonucleosides.

19. The aqueous mRNA composition of claim 17, wherein said deuterium-stabilised mRNA molecules comprise substitution of protium atoms by deuterium atoms.

20. The aqueous mRNA composition of claim 17, wherein said deuterium-stabilised mRNA molecules comprise a deuterium atom in the 2'OH-group on the ribose sugar moiety.

21. The aqueous mRNA composition of claim 14, wherein said deuterium-stabilised mRNA molecules display at least one of: i) increased structural integrity of their primary and/or secondary structure, compared to non-stabilized mRNA molecules; and ii) increased resistance to degradation compared to non-stabilised mRNA molecules.

22. The aqueous mRNA composition of claim 14, wherein said deuterium-stabilised mRNA molecules display increased resistance to at least one of (i) hydrolysis or degradation by endonucleases, and (ii) thermal degradation.

23. The aqueous mRNA composition of claim 14, wherein said deuterium-stabilised mRNA molecules display increased resistance to thermal hydrolysis after 1 day of exposure to 37° C.

24. The aqueous mRNA composition of claim 14, wherein said deuterium-stabilised mRNA molecules display increased resistance to thermal hydrolysis after a challenge at 45° C.

25. The aqueous mRNA composition of claim 14, wherein said deuterium-stabilised mRNA molecules are components of a vaccine.

26. The aqueous composition of claim 1, wherein synthesis comprises in vitro transcription in an aqueous composition comprising deuterium.

27. The aqueous composition of claim 1, wherein synthesis comprises incorporation of deuterium into the mRNA molecule via keto-enol tautomerization.

28. The aqueous composition of claim 1, wherein synthesis comprises in vitro transcription with deuterated ribonucleoside tri-phosphates (rNTPs).

29. The aqueous composition of claim 1, wherein synthesis consecutive steps of: (a) synthesising said deuterium-stabilised mRNA molecule by in vitro transcription in an aqueous composition comprising deuterium;
and (b) storing the synthesized mRNA molecule of step (a) in an aqueous solution comprising deuterium.

30. The aqueous composition of claim 1, wherein the deuterium-stabilised mRNA molecules are components of a RNA-based therapeutic.

31. The aqueous mRNA composition of claim 14, wherein the deuterium-stabilised mRNA molecules are components of a RNA-based therapeutic.

* * * * *